United States Patent
Kim et al.

(10) Patent No.: US 6,916,833 B2
(45) Date of Patent: Jul. 12, 2005

(54) SUBSTITUTED PIPERIDINES

(75) Inventors: Kyungjin Kim, Livingston, NJ (US); Emily Aijun Liu, Nutley, NJ (US); Steven Gregory Mischke, Florham Park, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/793,296

(22) Filed: Mar. 4, 2004

(65) Prior Publication Data

US 2004/0180929 A1 Sep. 16, 2004

Related U.S. Application Data

(60) Provisional application No. 60/454,387, filed on Mar. 13, 2003.

(51) Int. Cl.[7] ............... A61K 31/445; C07D 211/40; C07D 211/50; C07D 211/42
(52) U.S. Cl. .................... 514/328; 546/217
(58) Field of Search .................. 546/217; 514/328

(56) References Cited

FOREIGN PATENT DOCUMENTS

WO          WO 00/15657 A       3/2000

OTHER PUBLICATIONS

Leysen et al., Terahedron Letters, 38, pp. 2915–2198 (1997).

*Primary Examiner*—Rita Desai
(74) *Attorney, Agent, or Firm*—George W. Johnston; Patricia S. Rocha-Tramaloni

(57) ABSTRACT

The present invention provides compounds having formula (I):

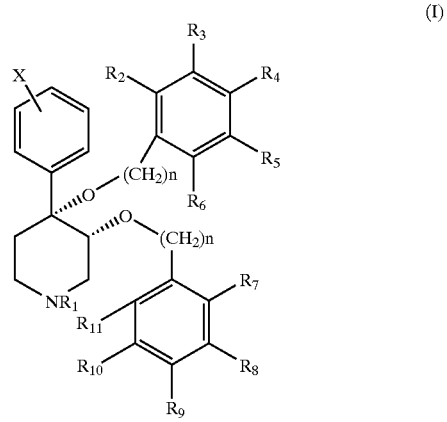

and formula (II):

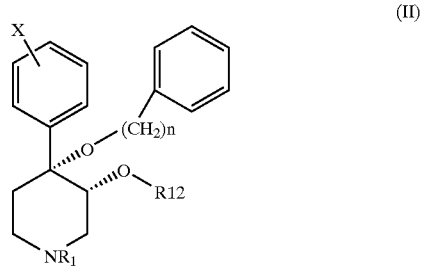

wherein X, n, and $R_1$–$R_{12}$ are defined herein, or a pharmaceutically acceptable salt thereof. The invention also provides a pharmaceutical composition comprising a therapeutically effective amount of a compound represented by formula (I) or (II) and a pharmaceutically acceptable carrier or excipient. The invention further provides a method for treating cancer comprising administering to a patient in need of such treatment a therapeutically effective amount of a compound represented by formula (I) or (II).

25 Claims, No Drawings

SUBSTITUTED PIPERIDINES

PRIORITY TO PROVISIONAL APPLICATION(S) UNDER 35 U.S.C. §119(e)

This application claims priority under 35 U.S.C. §119(e) of provisional application(s) Ser. No. 60/454,387, filed on Mar. 13, 2003.

FIELD OF THE INVENTION

The present invention provides a novel series of piperidines with cis-3,4-dialkoxy substitutions that are small molecule inhibitors of MDM2-p53 interaction. These compounds are useful in the treatment or control of cancer.

BACKGROUND OF THE INVENTION p53 is a tumor suppresser protein that plays a central role in protection against the development of cancer. p53 guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor, which is tightly regulated by MDM2 at the cellular level. MDM2 and p53 form a feedback control loop. MDM2 can bind p53 and inhibit its ability to trans-activate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention provides a compound represented by formula (I):

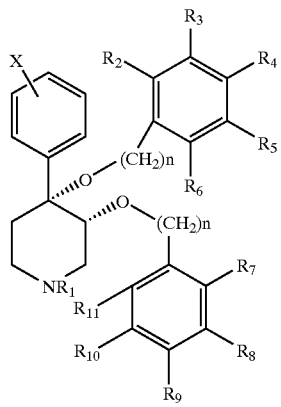

(I)

wherein
n is an integer independently selected from 1 or 2;
X is halogen;
$R_1$ is selected from the group consisting of hydrogen, carbonyl, sulfonyl, lower alkyl, and lower alkyl substituted by carbonyl, sulfonyl, or hydroxy;
$R_2$–$R_6$ are independently selected from the group consisting of hydrogen, halogen, lower alkyl, —C(CH$_3$)$_3$, CF$_3$, —OCH$_3$, —NO$_2$, and —CN; and
$R_7$–$R_{11}$ are independently selected from the group consisting of hydrogen, halogen, —CN, —NO$_2$, CF$_3$, —OCH$_3$, —COOCH$_3$, and —C$_6$H$_5$;
or a pharmaceutically acceptable salt thereof.

The present invention also provides a compound represented by formula (II):

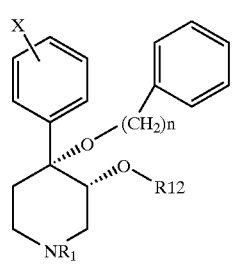

(II)

wherein
n is an integer from 1 to 2;
X is halogen;
$R_1$ is selected from the group consisting of hydrogen, carbonyl, sulfonyl, lower alkyl, and lower alkyl substituted by carbonyl, sulfonyl, or hydroxy; and
$R_{12}$ is selected from the group consisting of alkyl and alkenyl having from 1 to about 5 carbon atoms;
or a pharmaceutically acceptable salt thereof.

The invention also provides a pharmaceutical composition comprising a therapeutically effective amount of a compound represented by formula (I) or (II) and a pharmaceutically acceptable carrier or excipient. The invention further provides a method for treating cancer comprising administering to a patient in need of such treatment a therapeutically effective amount of a compound represented by formula (I) or (II).

DETAILED DESCRIPTION OF THE INVENTION

The present invention provides a novel series of small molecule inhibitors of MDM2-p53 interaction, piperidines with cis-3,4-dialkoxy substitutions, which have been tested in ELISA assays. The most potent compounds in this series have been shown to inhibit interaction of MDM2 protein with a p53-like peptide with a potency that is approximately the same as a p53-derived peptide. Binding of these compounds to the p53-binding pocket of MDM2 protein has been confirmed by NMR studies of selected compounds in this series as well as fragments of these compounds. These compounds have been shown to bind the same binding pockets as cis-imidazolines, which have demonstrated clear mechanistic activity in cell-based assays as well as antiproliferative activity against wild-type-p53 containing tumor cells both in vitro and in vivo. Therefore these compounds are useful as anticancer agents.

As used herein, the following terms have the given meanings:

"Alkenyl" means a straight-chain or branched aliphatic hydrocarbon having from 2 to 10, preferably 2 to 6 carbon atoms, and at least one carbon-carbon double bond, for example, vinyl, 2-butenyl, and 3-methyl-2-butenyl.

"Carbonyl" means a divalent —CO— radical.

"Effective amount" means an amount that is effective to prevent, alleviate or ameliorate symptoms of disease or prolong the survival of the subject being treated.

"Halogen" means fluorine, chlorine, bromine, or iodine.

"Hydroxy" means a monovalent —OH group.

"$IC_{50}$" means a concentration of a particular compound required to inhibit 50% of a specific measured activity. $IC_{50}$ can be measured, inter alia, as is described subsequently.

"Lower alkyl group" means a straight-chained or branched saturated aliphatic hydrocarbon. Typical lower alkyl groups include methyl, ethyl, propyl, and isopropyl.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Sulfonyl" means the bivalent radical —$SO_2$—.

"Therapeutically effective amount" means an amount of at least one compound of formula (I) or (II), or a pharmaceutically acceptable salt thereof, which significantly inhibits its proliferation and/or prevents differentiation of a human tumor cell, including human tumor cell lines.

Compounds of the present invention as exemplified advantageously show $IC_{50}$ values from about 3 µM to about 100 µM.

The compounds of the present invention are useful in the treatment or control of cell proliferative disorders, in particular, oncological disorders. These compounds and formulations containing the compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

In accordance with the present invention, a compound is provided represented by formula (I):

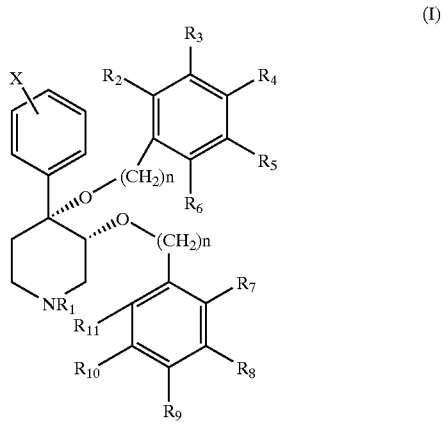

(I)

wherein
n is an integer independently selected from 1 or 2;
X is halogen;
$R_1$ is selected from the group consisting of hydrogen, carbonyl, sulfonyl, lower alkyl, and lower alkyl substituted by carbonyl, sulfonyl, or hydroxy;
$R_2$–$R_6$ are independently selected from the group consisting of hydrogen, halogen, lower alkyl, —$C(CH_3)_3$, $CF_3$, —$OCH_3$, —$NO_2$, and —CN; and
$R_7$–$R_{11}$ are independently selected from the group consisting of hydrogen, halogen, —CN, —$NO_2$, $CF_3$, —$OCH_3$, —$COOCH_3$, and —$C_6H_5$;

or a pharmaceutically acceptable salt thereof.

In a preferred embodiment of the invention, n is 1.

In another preferred embodiment of the invention, X is chloro or fluoro; more preferably chloro. In another preferred embodiment of the invention, X is a para substituent.

In another preferred embodiment of the invention, $R_1$ is selected from the group consisting of hydrogen, —$CH_2CH_3$, —$CH_2CH_2CH_3$, —$COCH_3$, —$COCH_2CH_3$, —$CH_2CHOHCH_2OH$, and —$SO_2CH_3$; more preferably $R_1$ is hydrogen.

In another preferred embodiment of the invention, $R_2$ and $R_6$ are independently selected from the group consisting of hydrogen and halogen; more preferably hydrogen, fluoro, chloro, and bromo.

In another preferred embodiment of the invention, $R_3$ and $R_5$ are independently selected from the group consisting of hydrogen, fluoro, chloro, bromo, —$CH_3$, —$OCH_3$, —$CN$, and —$NO_2$; more preferably $R_3$ and $R_5$ are independently selected from the group consisting of hydrogen, fluoro, chloro, and bromo.

In another preferred embodiment of the invention, $R_4$ is selected from the group consisting of hydrogen, fluoro, chloro, bromo, —$C(CH_3)_3$, —$CH_3$, —$CN$, and —$CF_3$; more preferably $R_4$ is selected from the group consisting of hydrogen, fluoro, chloro, and bromo.

In another preferred embodiment of the invention, $R_7$ and $R_{11}$ are independently selected from the group consisting of hydrogen, halogen, —$CN$, —$NO_2$, and —$C_6H_5$; more preferably $R_7$ and $R_{11}$ are independently selected from the group consisting of hydrogen, fluoro, chloro, and bromo.

In another preferred embodiment of the invention, $R_8$ and $R_{10}$ are independently selected from the group consisting of hydrogen, fluoro, chloro, bromo, —$CN$, —$NO_2$, and —$OCH_3$; more preferably $R_8$ and $R_{10}$ are independently selected from the group consisting of hydrogen, fluoro, chloro, and bromo.

In another preferred embodiment of the invention, $R_9$ is selected from the group consisting of hydrogen, fluoro, chloro, bromo, —$OCH_3$, —$CN$, —$CF_3$, and —$COOCH_3$; more preferably $R_9$ is selected from the group consisting of hydrogen, fluoro, chloro, and bromo.

Preferred compounds having formula (I) include:

cis-[rac]-4-Benzyloxy-4-(4-chloro-phenyl)-3-(3,4-difluoro-benzyloxy)-piperidine;

cis-[rac]-4-Benzyloxy-4-(4-chloro-phenyl)-3-(2,6-difluoro-benzyloxy)-piperidine;

cis-[rac]-4-Benzyloxy-3-(biphenyl-2-ylmethoxy)-4-(4-chloro-phenyl)-piperidine;

cis-[rac]-4-[4-Benzyloxy-4-(4-chloro-phenyl)-piperidin-3-yloxymethyl]-benzonitrile;

cis-[rac]-4-Benzyloxy-4-(4-chloro-phenyl)-3-(3-nitro-benzyloxy)-piperidine;

cis-[rac]-4-Benzyloxy-3-(3-bromo-benzyloxy)-4-(4-chloro-phenyl)-piperidine;

cis-[rac]-4-Benzyloxy-4-(4-chloro-phenyl)-3-(2,4-difluoro-benzyloxy)-piperidine;

cis-[rac]-4-Benzyloxy-3-(2-chloro-4-fluoro-benzyloxy)-4-(4-chloro-phenyl)-piperidine;

cis-[rac]-4-[4-Benzyloxy-4-(4-chloro-phenyl)-piperidin-3-yloxymethyl]-benzoic acid methyl ester;

cis-[rac]-4-Benzyloxy-4-(4-chloro-phenyl)-3-(3,5-difluoro-benzyloxy)-piperidine;

cis-[rac]-4-Benzyloxy-3-(3-chloro-2-fluoro-benzyloxy)-4-(4-chloro-phenyl)-piperidine;

cis-[rac]-4-Benzyloxy-4-(4-chloro-phenyl)-3-(2,5-dichloro-benzyloxy)-piperidine;

cis-[rac]-4-Benzyloxy-4-(4-chloro-phenyl)-3-(2,3-difluoro-benzyloxy)-piperidine;

cis-[rac]-4-Benzyloxy-4-(4-chloro-phenyl)-3-(4-trifluoromethyl-benzyloxy)-piperidine;

cis-[rac]-4-Benzyloxy-4-(4-chloro-phenyl)-3-(4-fluoro-benzyloxy)-piperidine;

cis-[rac]-4-Benzyloxy-3-(4-bromo-benzyloxy)-4-(4-chloro-phenyl)-piperidine;

cis-[rac]-4-Benzyloxy-4-(4-chloro-phenyl)-3-(3-fluoro-benzyloxy)-piperidine;

cis-[rac]-2-[4-Benzyloxy-4-(4-chloro-phenyl)-piperidin-3-yloxymethyl]-benzonitrile;

cis-[rac]-3-[4-Benzyloxy-4-(4-chloro-phenyl)-piperidin-3-yloxymethyl]-benzonitrile;

cis-[rac]-4-Benzyloxy-4-(4-chloro-phenyl)-3-(4,5-dimethoxy-2-nitro-benzyloxy)-piperdine;

cis-[rac]-4-Benzyloxy-3-but-2-enyloxy-4-(4-chloro-phenyl)-piperidine;

cis-[rac]-4-Benzyloxy-4-(4-chloro-phenyl)-3-pent-2-enyloxy-piperidine;

cis-[rac]-4-Benzyloxy-4-(4-chloro-phenyl)-3-(2,3,6-trifluoro-benzyloxy)-piperidine;

cis-[rac]-4-Benzyloxy-3-butoxy-4-(4-chloro-phenyl)-piperidine;

cis-[rac]-4-Benzyloxy-3-(4-chloro-2-fluoro-benzyloxy)-4-(4-chloro-phenyl)-piperidine;

cis-[rac]-4-Benzyloxy-3-(4-bromo-2-fluoro-benzyloxy)-4-(4-chloro-phenyl)-piperidine;

cis-[rac]-4-Benzyloxy-4-(4-chloro-phenyl)-3-(2,4,6-trifluoro-benzyloxy)-piperidine;

cis-[rac]-4-Benzyloxy-4-(4-chloro-phenyl)-3-(2,4,5-trifluoro-benzyloxy)-piperidine;

cis-[rac]-4-Benzyloxy-4-(4-chloro-phenyl)-3-(2,3,4-trifluoro-benzyloxy)-piperidine;

cis-[rac]-3-Benzyloxy-4-(4-chloro-phenyl)-4-(2,4,6-trifluoro-benzyloxy)-piperidine;

cis-[rac]-3-Benzyloxy-4-(4-chloro-phenyl)-4-(2,5-dichloro-benzyloxy)-piperidine;

cis-[rac]-3-Benzyloxy-4-(4-chloro-phenyl)-4-(2,6-dichloro-benzyloxy)-piperidine;

cis-[rac]-3-Benzyloxy-4-(4-chloro-phenyl)-4-(2,6-difluoro-benzyloxy)-piperidine;

cis-[rac]-3-Benzyloxy-4-(4-chloro-phenyl)-4-(3-methoxy-benzyloxy)-piperidine;

cis-[rac]-3-Benzyloxy-4-(4-chloro-phenyl)-4-(2,3,6-trifluoro-benzyloxy)-piperidine;

cis-[rac]-3-Benzyloxy-4-(4-chloro-phenyl)-4-(2-fluoro-benzyloxy)-piperidine;

cis-[rac]-3-Benzyloxy-4-(4-chloro-phenyl)-4-(2-fluoro-3-methyl-benzyloxy)-piperidine;

cis-[rac]-4-(4-Chloro-phenyl)-3-(3,4-dichloro-benzyloxy)-4-(4-fluoro-benzyloxy)-piperidine;

cis-[rac]-4-(4-Bromo-benzyloxy)-4-(4-chloro-phenyl)-3-(3,4-dichloro-benzyloxy)-piperidine;

cis-[rac]-4-(4-Chloro-phenyl)-3-(3,4-dichloro-benzyloxy)-4-(2,4-difluoro-benzyloxy)-piperidine;

cis-[rac]-4-(2-Chloro-4-fluoro-benzyloxy)-4-(4-chloro-phenyl)-3-(3,4-dichloro-benzyloxy)-piperidine;

cis-[rac]-4-(2-Bromo-benzyloxy)-4-(4-chloro-phenyl)-3-(3,4-dichloro-benzyloxy)-piperidine;

cis-[rac]-4-(4-tert-Butyl-benzyloxy)-4-(4-chloro-phenyl)-3-(3,4-dichloro-benzyloxy)-piperidine;

cis-[rac]-4-[4-(4-Chloro-phenyl)-3-(3,4-dichloro-benzyloxy)-piperidin-4-yloxymethyl]-benzonitrile;

cis-[rac]-4-(3-Chloro-benzyloxy)-4-(4-chloro-phenyl)-3-(3,4-dichloro-benzyloxy)-piperidine;

cis-[rac]-4-(3-Bromo-benzyloxy)-4-(4-chloro-phenyl)-3-(3,4-dichloro-benzyloxy)-piperidine;

cis-[rac]-4-(4-Chloro-phenyl)-3-(3,4-dichloro-benzyloxy)-4-(2-fluoro-benzyloxy)-piperidine;

cis-[rac]-4-(4-Chloro-phenyl)-3-(3,4-dichloro-benzyloxy)-4-(3,5-difluoro-benzyloxy)-piperidine;
cis-[rac]-4-(3-Chloro-2-fluoro-benzyloxy)-4-(4-chloro-phenyl)-3-(3,4-dichloro-benzyloxy)-piperidine;
cis-[rac]-4-(4-Chloro-phenyl)-3-(3,4-dichloro-benzyloxy)-4-(2,3-difluoro-benzyloxy)-piperidine;
cis-[rac]-4-(4-Chloro-phenyl)-3-(3,4-dichloro-benzyloxy)-4-(4-trifluoromethyl-benzyloxy)-piperidine;
cis-[rac]-4-(4-Chloro-phenyl)-3-(3,4-dichloro-benzyloxy)-4-(3-fluoro-benzyloxy)-piperidine;
cis-[rac]-3-[4-(4-Chloro-phenyl)-3-(3,4-dichloro-benzyloxy)-piperidin-4-yloxymethyl]-benzonitrile;
cis-[rac]-4-(2-Chloro-benzyloxy)-4-(4-chloro-phenyl)-3-(3,4-dichloro-benzyloxy)-piperidine;
cis-[rac]-4-(4-Chloro-phenyl)-3-(3,4-dichloro-benzyloxy)-4-(4-methyl-benzyloxy)-piperidine;
cis-[rac]-4-(4-Chloro-phenyl)-3,4-bis-(2,4-difluoro-benzyloxy)-piperidine;
cis-[rac]-4-(4-Chloro-phenyl)-3,4-bis-(3-nitro-benzyloxy)-piperidine;
cis-[rac]-1-[4-Benzyloxy-4-(4-chloro-phenyl)-3-(2,4-difluoro-benzyloxy)-piperidin-1-yl]-ethanone;
cis-[rac]-1-[4-Benzyloxy-3-(3-bromo-benzyloxy)-4-(4-chloro-phenyl)-piperidin-1-yl]-ethanone;
cis-[rac]-1-[4-Benzyloxy-3-(2-chloro-4-fluoro-benzyloxy)-4-(4-chloro-phenyl)-piperidin-1-yl]-ethanone;
cis-[rac]-1-[4-Benzyloxy-4-(4-chloro-phenyl)-3-(3,5-difluoro-benzyloxy)-piperidin-1-yl]-ethianone;
cis-[rac]-1-[4-Benzyloxy-3-(3-chloro-2-fluoro-benzyloxy)-4-(4-chloro-phenyl)-piperidin-1-yl]-ethanone;
cis-[rac]-1-[4-Benzyloxy-4-(4-chloro-phenyl)-3-(3,4-dichloro-benzyloxy)-piperidin-1-yl]-ethanone;
cis-[rac]-1-[4-Benzyloxy-4-(4-chloro-phenyl)-3-(4-fluoro-benzyloxy)-piperidin-1-yl]-ethanone;
cis-[rac]-1-[4-Benzyloxy-3-(4-bromo-benzyloxy)-4-(4-chloro-phenyl)-piperidin-1-yl]-ethanone;
cis-[rac]-1-[4-Benzyloxy-4-(4-chloro-phenyl)-3-(3-fluoro-benzyloxy)-piperidin-1-yl]-ethanone;
cis-[rac]-3-[1-Acetyl-4-benzyloxy-4-(4-chloro-phenyl)-piperidin-3-yloxymethyl]-benzonitrile;
cis-[rac]-1-[4-Benzyloxy-4-(4-chloro-phenyl)-3-(2,6-difluoro-benzyloxy)-piperidin-1-yl]-ethanone;
cis-[rac]-1-[4-Benzyloxy-4-(4-chloro-phenyl)-3-(3-nitro-benzyloxy)-piperidin-1-yl]-ethanone;
cis-[rac]-1-[4-Benzyloxy-4-(4-chloro-phenyl)-3-(2,3,4-trifluoro-benzyloxy)-piperidin-1-yl]-ethanone;
cis-[rac]-1-[4-(4-Chloro-phenyl)-3-(3,4-dichloro-benzyloxy)-4-(2-fluoro-benzyloxy)-piperidin-1-yl]-ethanone;
cis-[rac]-1-[4-Benzyloxy-4-(4-chloro-phenyl)-3-(2,3,4-trifluoro-benzyloxy)-piperidin-1-yl]-propan-1-one;
cis-[rac]-1-[4-Benzyloxy-4-(4-chloro-phenyl)-3-(3,4-dichloro-benzyloxy)-piperidin-1-yl]-propan-1-one;
cis-[rac]-4-Benzyloxy-3-(4-bromo-benzyloxy)-4-(4-fluoro-phenyl)-piperidine;
cis-[rac]-4-Benzyloxy-4-(4-chloro-phenyl)-3-(3,4-dichloro-benzyloxy)-1-ethyl-piperidine;
cis-[rac]-4-Benzyloxy-4-(4-chloro-phenyl)-3-(3,4-dichloro-benzyloxy)-1-propyl-piperidine;
cis-[rac]-3-[4-Benzyloxy-4-(4-chloro-phenyl)-3-(2,3,4-trifluoro-benzyloxy)-piperidin-1-yl]-propane-1,2-diol;
cis-[rac]-3-[4-Benzyloxy-3-(4-bromo-benzyloxy)-4-(4-chloro-phenyl)-piperidin-1-yl]-propane-1,2-diol; and
cis-[rac]-3-[4-Benzyloxy-4-(4-chloro-phenyl)-3-(2,3,4-trifluoro-benzyloxy)-piperidin-1-yl]-methane sulfonyl.

Further in accordance with the present invention, a compound is provided having formula (II):

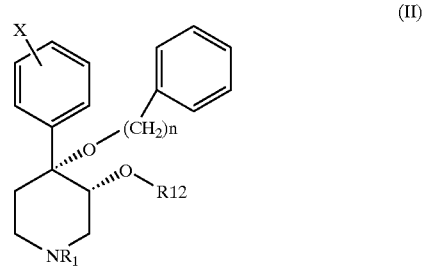

(II)

wherein n is an integer from 1 to 2;

X is halogen;

$R_1$ is selected from the group consisting of hydrogen, carbonyl, sulfonyl, lower alkyl, and lower alkyl substituted by carbonyl, sulfonyl, or hydroxy; and $R_{12}$ is selected from the group consisting of alkyl and alkenyl having from 1 to about 5 carbon atoms;

or a pharmaceutically acceptable salt thereof.

In a preferred embodiment of the invention, n is 1.

In another preferred embodiment of the invention, X is chloro or fluoro; more preferably chloro. In another preferred embodiment of the invention, X is apara substituent.

In another preferred embodiment of the invention, $R_1$ is selected from the group consisting of hydrogen, —$CH_2CH_3$, —$CH_2CH_2CH_3$, —$COCH_3$, —$COCH_2CH_3$, —$CH_2CHOHCH_2OH$, and —$SO_2CH_3$; more preferably $R_1$ is hydrogen.

In another preferred embodiment of the invention, $R_{12}$ is selected from the group consisting of —$(CH_2)_3CH_3$, —$(CH_2)_4CH_3$, —$CH_2CH=CHCH_3$, and —$CH_2CH=CHCH_2CH_3$.

Preferred compounds having formula (II) include:
cis-[rac]-4-Benzyloxy-4-(4-fluoro-phenyl)-3-butyloxy-piperidine;
cis-[rac]-4-Benzyloxy-4-(4-fluoro-phenyl)-3-pentyloxy-piperidine;
cis-[rac]-4-Benzyloxy-4-(4-fluoro-phenyl)-3-(but-2-en)yloxy-piperidine; and
cis-[rac]-4-Benzyloxy-4-(4-fluoro-phenyl)-3-(pent-2-enyl)oxy-piperidine.

Other preferred compounds having formula (II) include:
cis-[rac]-4-Benzyloxy-4-(4-chloro-phenyl)-3-butyloxy-piperidine;
cis-[rac]-4-Benzyloxy-4-(4-chloro-phenyl)-3-pentyloxy-piperidine;
cis-[rac]-4-Benzyloxy-4-(4-chloro-phenyl)-3-(but-2-en)yloxy-piperidine; and
cis-[rac]-4-Benzyloxy-4-(4-chloro-phenyl)-3-(pent-2-enyl)oxy-piperidine.

The invention also provides a pharmaceutical composition comprising a therapeutically effective amount of a compound represented by formula (I) or (II) and a pharmaceutically acceptable carrier or excipient. The invention further provides a method for treating cancer comprising administering to a patient in need of such treatment a therapeutically effective amount of a compound represented by formula (I) or (II). Preferably, the cancer is breast or colon cancer.

The compounds of the present invention, and intermediates thereof, can be prepared according to the schemes set out below. Starting materials are made using known procedures or as illustrated. The abbreviations used in the descriptions of the schemes, preparations, and the examples are set out below.

ACE-Cl=1-chloroethyl chloroformate (Aldrich)
BEMP=2-tert-butylimino-2-diethylamino-1,3-dimethyl-perhydro-1,3,2-diazaphosphorine (Fluka)
Boc=tert-butyloxycarbonyl
t-BuOK=potassium tert-butoxide
$CH_2Cl_2$=dichloromethane
DCE=1,2-dichloroethane
DMF=N,N-dimethylformamide
$Et_2O$=diethyl ether
EtOH=ethanol
$H_2SO_4$=sulfuric acid
HCl=hydrogen chloride
$H_2O$=water
MeOH=methanol
NaH=sodium hydride
NMO=N-methylmorpholine-N-oxide
NMP=1-methyl-2-pyrrolidinone
$OSO_4$=osmium tetroxide
Polymer (supported) BEMP=2-tert-butylimino-2-diethylamino-1,3-dimethyl-perhydro-1,3,2-diazaphosphorine supported by polystyrene resin (Fluka)
i-$Pr_2$NEt=N, N-diisopropylethylamine
TEA=triethylamine
TFA=trifluoroacetic acid
THF=tetrahydrofuran Schemes 1–3 outline a general method for preparing compounds of the invention having formula (I) and (II) using a novel solid phase synthesis. Scheme 4 outlines a general method for preparing the compounds in solution phase. Scheme 5 illustrates various methods for modifying the $R_1$ group using a novel polymer supported reagent.

In Scheme 1, the protection of a secondary amine of a commercially available 4-aryl-1,2,3,6-tetrahydropyridine is outlined. The preferred protecting group is a tert-butyloxycarbonyl, which can be synthesized from known procedures (Greene, T. W. and Wuts, P. G. M, $2^{nd}$ Edition, John Wiley & Sons, N.Y. 1991). For liquid phase synthesis, the resulting tert-butyl ester can be treated with $OsO_4$/NMO to form the dihydroxy intermediate A. Selective o-alkylation of intermediate A at C3 can be carried out using NaH and 4-methoxybenzyl chloride. The resulting intermediate can be benzylated according to known methods. Deprotection of both 4-methoxylbenzyl and tert-butyloxycarbonyl groups using 50% TFA/$CH_2Cl_2$ yields 4-aryl-4-benzyloxy-3-hydroxypiperidine B. For solid phase synthesis, the resulting piperidine B can be coupled to a suitable linker, such as a chloromethyl derivative ArgoPore-Cl linker (Argonaut). Alkylation on solid phase can be accomplished using t-BuOK to generate the anion followed by coupling with various alkyl halides (RX). The final reaction product can be cleaved from the N-benzyl linked tertiary amine linker using alpha-chloroethyl chloroformat (ACE-Cl)/MeOH to give the piperidine compounds of the invention (Leysen, D. et al. *Tetrahedron Lett.* 1997, 2915–2918).

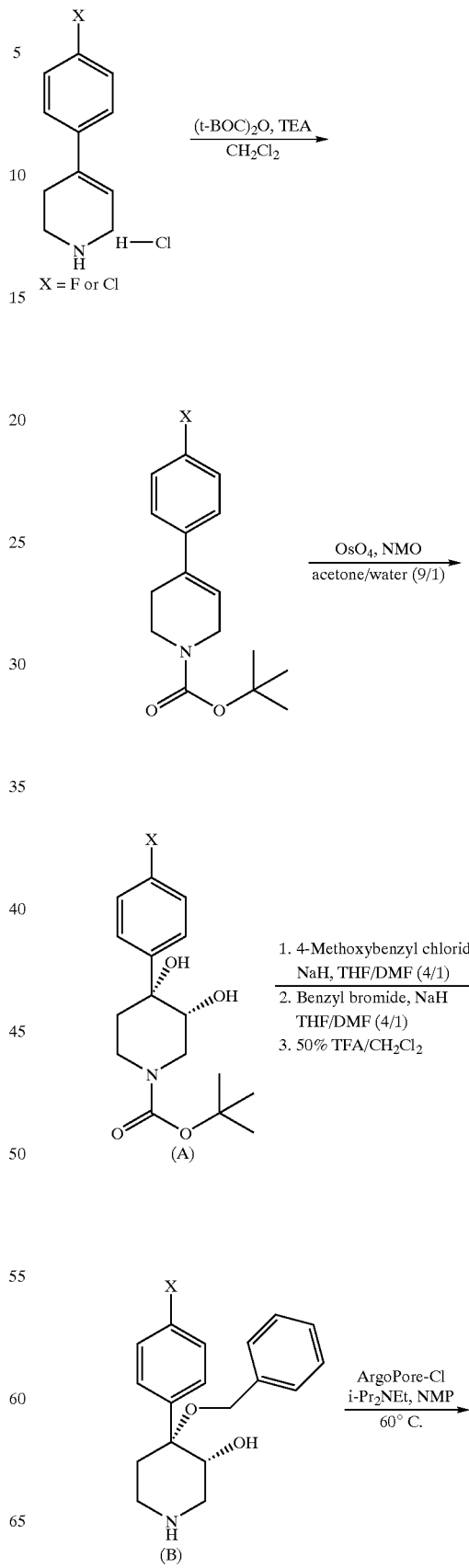

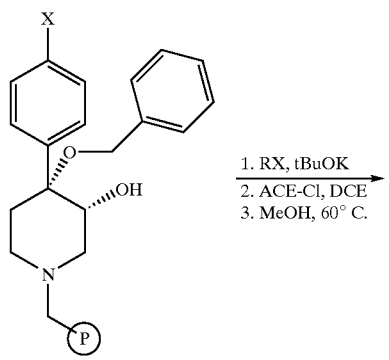
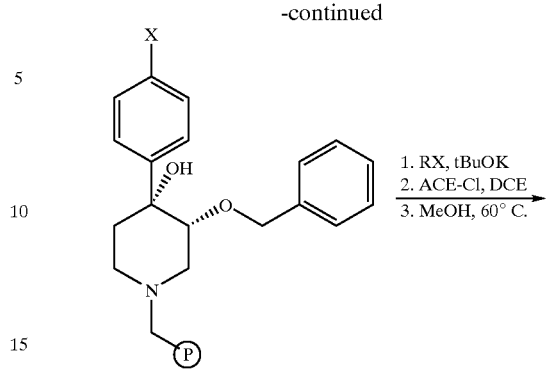

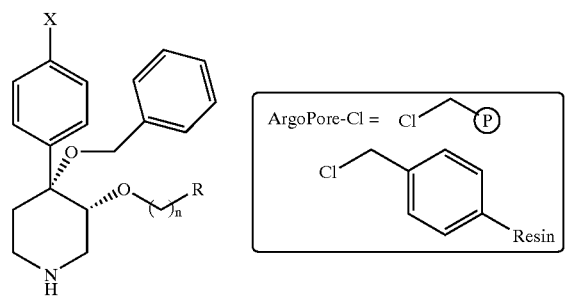

In Scheme 2, a general method is outlined for preparing compounds of formula (I) that feature functionalized R groups derived from intermediate A in Scheme 1. Intermediate A can be converted to 4-aryl-3-benzyloxy-3-hydroxypiperidine via alkylation at C3 using NaH and benzylbromide followed by acidic deprotection of a tert-butyloxycarbonyl group. The subsequent synthesis on solid phase can be accomplished to yield the piperidine compounds of the invention following the described reactions set out in Scheme 1.

Scheme 2

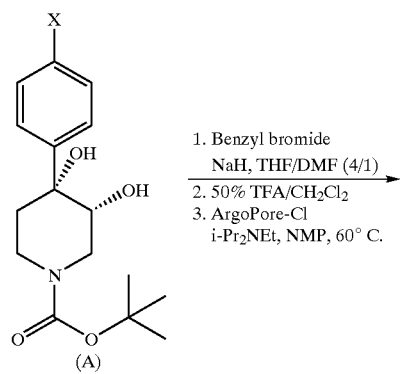

In Scheme 3, deprotection of a tert-butyloxycarbonyl from intermediate A can be carried out using 50% TFA/CH$_2$Cl$_2$. The synthesis on solid phase commences with the coupling of the resulting 4-aryl-3,4-dihydroxypiperidine with a ArgoPore-Cl linker. Dialkylation using t-BuOK and alkyl halides (RX) followed by cleavage of the polymer support according to the described conditions affords the piperidine compounds of the invention.

Scheme 3

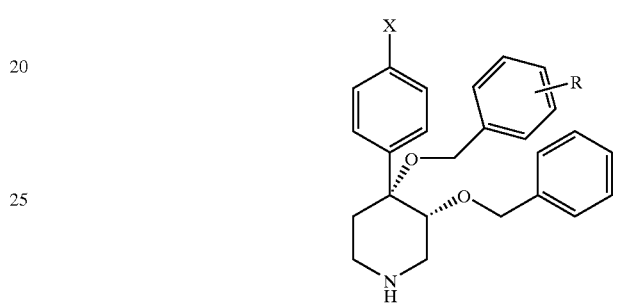
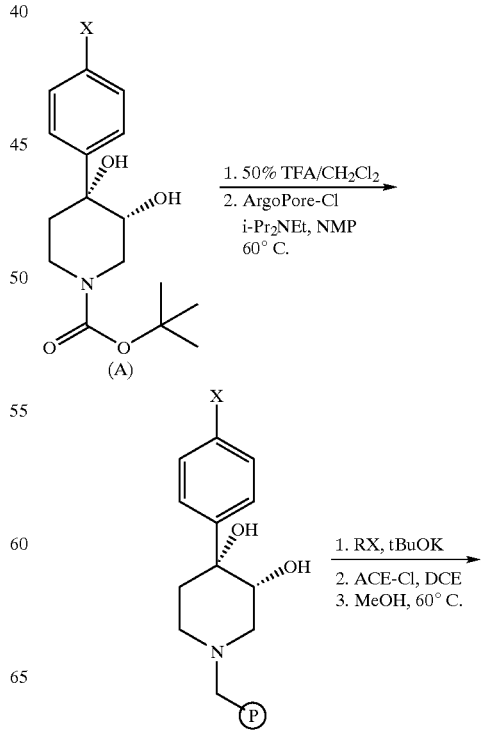

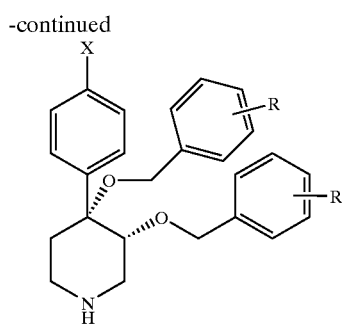

In Scheme 4, a general synthetic method is outlined for preparing compounds of formula (I) and (II) in solution phase. Sequential alkylation of intermediate A using NaH and alkyl halides followed by acidic deprotection of tert-butyloxycarbonyl provides the piperidine compounds of the invention.

Scheme 4

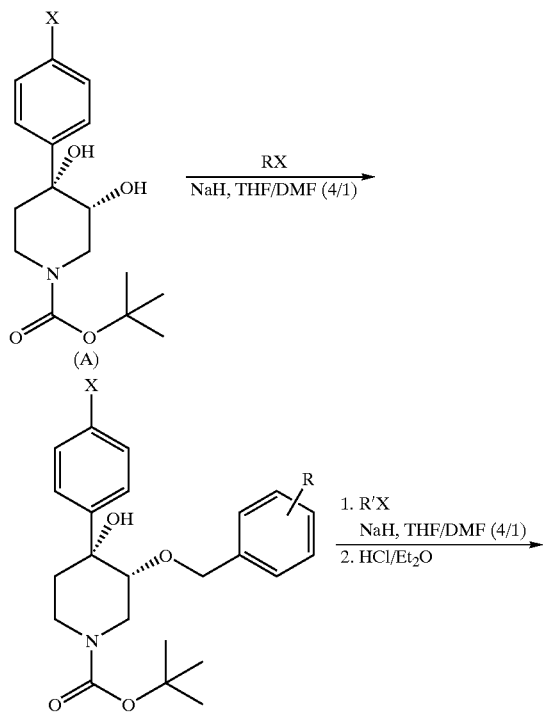

In Scheme 5, a general method is outlined for the post-modification of intermediate C. The secondary amine of intermediate C can be treated with a variety of agents such as acyl chlorides, alkyl halides, and sulfonyl chlorides to form the corresponding amide, tert-amine, or sulfonamide. The intermediate C can also be allylated using polymer support BEMP and allyl iodide to form the N-allyl substituted intermediate, which can be further treated with $OsO_4$/NMO to form 3-propane-1,2-diol-substituted piperidines of the invention.

Scheme 5

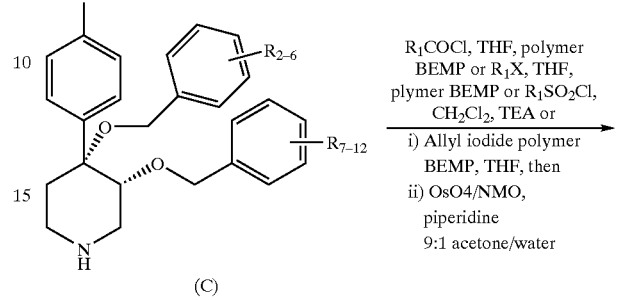

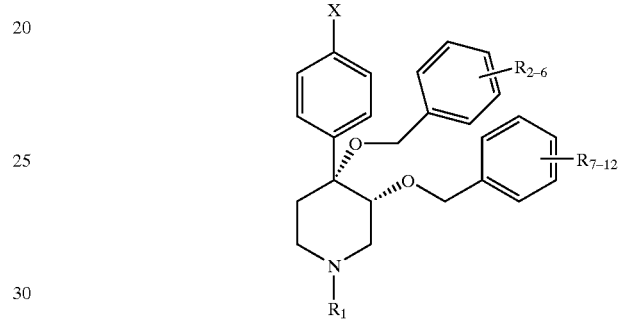

The compounds of the present invention can be prepared according to the examples below. The examples are presented for purposes of demonstrating, but not limiting, the preparation of the compounds and compositions of this invention.

EXAMPLES

The inhibitory activity ($IC_{50}$) of the compounds prepared in the examples below, and represented by formula (I) or (II), is in the range of 3 μM to 100 μM.

Example 1 cis-[rac]-4-(4-Chlorophenyl)-3,4-dihydroxypiperidine-1-carboxylic acid tert-butyl ester

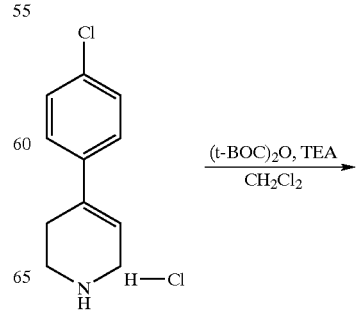

-continued

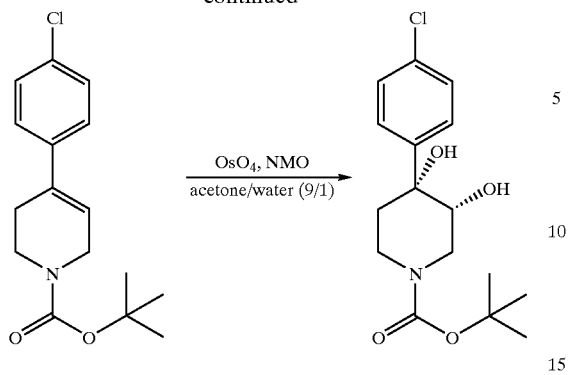

4-(4-Chlorophenyl)-1,2,3,6-tetrahydropyridine hydrochloride (Lancaster, 1.00 g, 4.35 mmol), triethylamine (0.92 g, 9.13 mmol), and di-tert-butyl carbonate (Aldrich, 1.04 g, 4.78 mmol) were combined in dichloromethane (100 mL) and stirred at room temperature for 14 hours. The mixture was washed with saturated aqueous ammonium chloride solution (30 mL), water (30 mL), saturated sodium chloride solution (30 mL) and dried over anhydrous magnesium sulfate. The mixture was filtered and concentrated in vacuo to give 4-(4-chlorophenyl)-3,6-dihydro-2H-pyridine-1-carboxylic acid tert-butyl ester (1.41 g, 100%) of as a viscous yellow oil, which was used without further purification. 4-(4-Chlorophenyl)-3,6-dihydro-2H-pyridine-1-carboxylic acid tert-butyl ester (334 mg, 1.14 mmoL) was dissolved in acetone/water (1:1, 10 mL), and N-methylmorpholine-N-oxide (Aldrich, 462 mg, 3.42 mmoL) and a catalytic amount of osmium tetroxide (Aldrich) were added. The mixture was stirred at room temperature for 3 hours. A saturated aqueous solution of sodium sulfite (2 mL) was added, and the mixture was stirred for 30 minutes at room temperature. The mixture was diluted with ethyl acetate (10 mL) and water (5 mL). The organic layer was separated, and the aqueous layer was extracted with ethyl acetate (2×10 mL). The combined organic layers were washed with brine and dried over anhydrous magnesium sulfate. The mixture was filtered and concentrated in vacuo to give cis-[rac]-4-(4-chlorophenyl)-3,4-dihydroxypiperidine-1-carboxylic acid tert-butyl ester (364 mg, 1.11 mmol, 97%) as a yellow oil.

Example 2 cis-[rac]-4-(4-Chlorophenyl)-3-(3,4-dichlorobenzyloxy)-4-hydroxypiperidine-1-carboxylic acid tert-butyl ester To an ice-cold suspension of sodium hydride (62 mg, 2.6 mmoL) in a mixture of tetrahydrofuran/N,N-dimethylformamide (4/1, 4 mL) was added dropwise a solution of cis-[rac]-4-(4-chlorophenyl)-3,4-dihydroxypiperidine-1-carboxylic acid tert-butyl ester (Example 1, 340 mg, 1.04 mmol) in tetrahydrofuran/N,N-dimethylformamide (1 mL, 4/1). After the addition was complete, the mixture was stirred with ice cooling for 15 minutes. Then 3,4-dichlorobenzyl chloride (Aldrich, 239 mg, 1.14 mmol) was added, and the mixture was warmed to room temperature and stirred for 20 hours. The mixture was poured into a saturated aqueous solution of ammonium chloride (30 mL), and the mixture was extracted with ethyl acetate (3×15 mL). The combined organic layers were washed with water (2×20 mL), saturated aqueous sodium chloride solution (1×20 mL), and dried over anhydrous magnesium sulfate. The mixture was filtered and concentrated in vacuo to give a viscous oil (500 mg), which was purified by flash silica gel chromatography (Merck silica gel 60, 230 to 400 mesh) to afford cis-[rac]-4-(4-chlorophenyl)-3-(3,4-dichlorobenzyloxy)-4-hydroxypiperidine-1-carboxylic acid tert-butyl ester (310 mg, 61%) as a colorless oil.

Example 3 cis-[rac]-4-(Benzyloxy)-4-(4-chlorophenyl)-3-(3,4-dichlorobenzyloxy)-piperidine-1-carboxylic acid tert-butyl ester

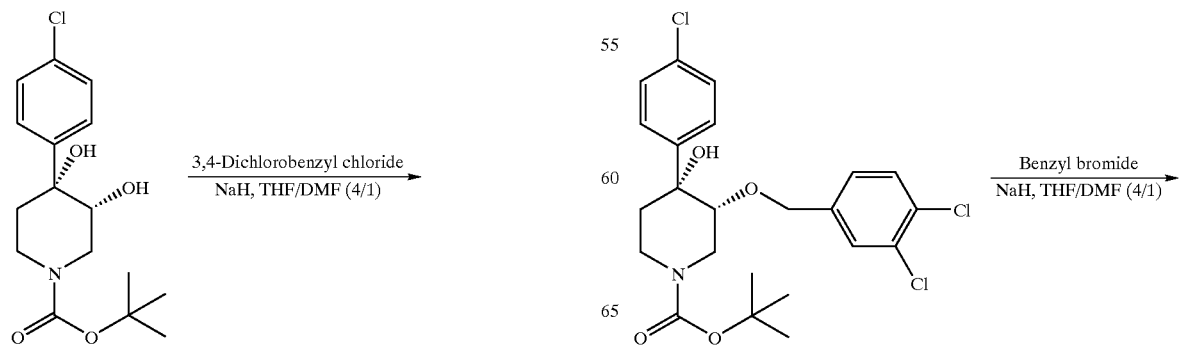

-continued

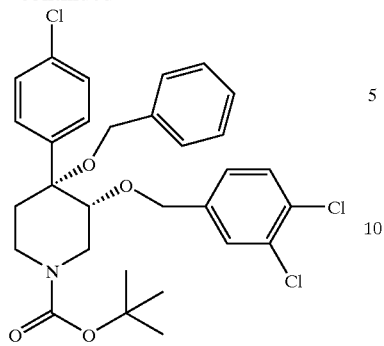

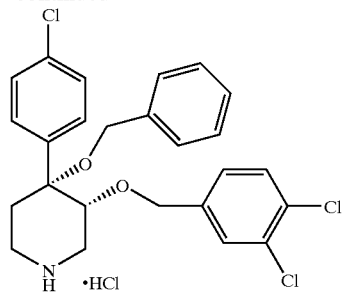

To an ice cold solution of cis-[rac]-4-(4-chlorophenyl)-3-(3,4-dichloro-benzyloxy)-4-hydroxypiperidine-1-carboxylic acid tert-butyl ester (Example 2, 224 mg, 0.46 mmol) in tetrahydrofuran (1.5 mL) was added sodium hydride (22 mg, 0.92 mmol) portionwise. After stirring with ice cooling for ten minutes, benzyl bromide (86 mg, 0.51 mmol) was added followed by N,N-dimethylformamide (0.5 mL). The cooling bath was removed, and the mixture was warmed to room temperature and stirred for 3 hours. Several drops of methanol were added, and the mixture was stirred and room temperature for 1 hour. The mixture was partitioned between ethyl acetate (30 mL) and saturated aqueous ammonium chloride solution (15 mL). The organic layer was separated, and the aqueous layer was extracted with ethyl acetate (3×15 mL). The combined organic layers were washed with water (3×30 mL), saturated aqueous sodium chloride solution (15 mL) and dried over anhydrous magnesium sulfate. The mixture was filtered and concentrated in vacuo to give cis-[rac]-4-(benzyloxy)-4-(4-chlorophenyl)-3-(3,4-dichlorobenzyloxy)-piperidine-1-carboxylic acid tert-butyl ester (240 mg), which was used without futher purification.

Example 4 cis-[rac]-4-(Benzyloxy)-4-(4-chlorophenyl)-3-(3,4-dichlorobenzyloxy)-piperidine hydrochloride

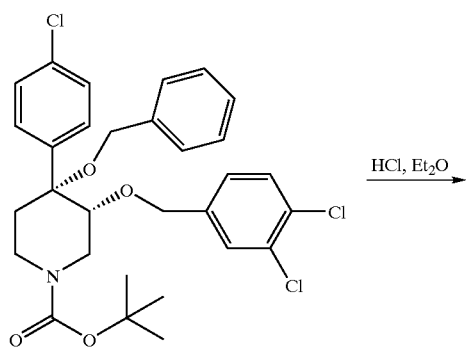

Crude cis-[rac]-4-(benzyloxy)-4-(4-chlorophenyl)-3-(3,4-dichlorobenzyloxy)-piperidine-1-carboxylic acid tert-butyl ester (Example 3, 240 mg) was dissolved in anhydrous diethyl ether (10 mL). The mixture was cooled in an ice bath, and hydrogen chloride gas was passed through the solution for 10 minutes. The reaction vessel was tightly stoppered and stored at 0° C. for 24 hours. The precipitated solid was collected and washed with diethyl ether to afford cis-[rac]-4-(benzyloxy)-4-(4-chlorophenyl)-3-(3,4-dichlorobenzyloxy)-piperidine hydrochloride as a white solid (130 mg, 55%). HR-FAB m/e calcd for $C_{24}H_{24}NO_2Cl$: $[M+H]^+$ 476.0952, found 476.0931.

Example 5 cis-[rac]-4-Benzyloxy-4-(4-chloro-phenyl)-3-(4-methoxy-benzyloxy)-piperidine-1-carboxylic acid tert-butyl ester

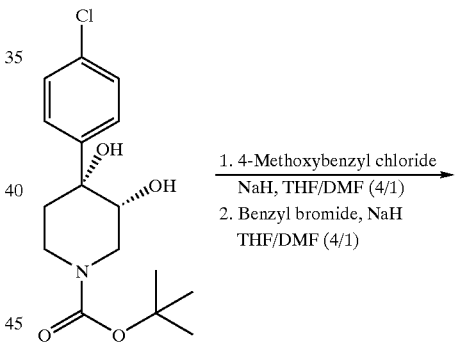

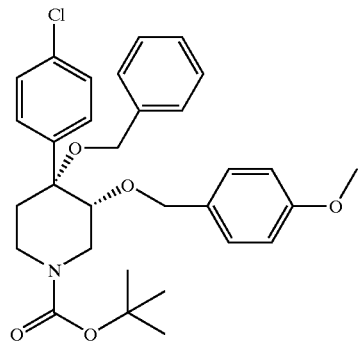

cis-[rac]-4-Benzyloxy-4-(4-chloro-phenyl)-3-(4-methoxy-benzyloxy)-piperidine-1-carboxylic acid tert-butyl ester was prepared from cis-[rac]-4-(4-chlorophenyl)-3,4-dihydroxypiperidine-1-carboxylic acid tert-butyl ester (Example 1) and 4-methoxybenzyl chloride (Aldrich) following the procedures used in Examples 2 and 3, which was used without purification.

Example 6 cis-[rac]-4,4-[benzyloxy-(4-chlorophenyl)]-3-hydroxypiperidine

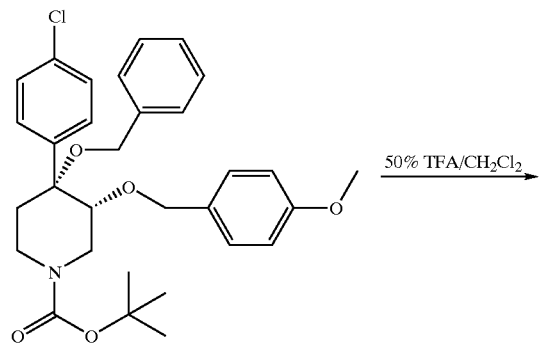

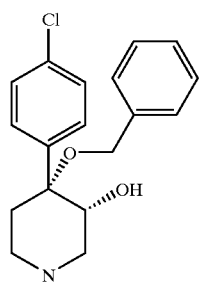

Molecular Weight = 317.81 cis-[rac]-4-Benzyloxy-4-(4-chloro-phenyl)-3-(4-methoxy-benzyloxy)-piperidine-1-carboxylic acid tert-butyl ester (Example 5, 550 mg, 1.02 mmol) was dissolved in 50% trifluoroacetic acid/dichloromethane (10 mL). After stirring 1.5 hours, the solution was evaporated in vacuo. The residue was triturated in 1:1 ethyl acetate/hexane to provide cis-[rac]-4,4-[benzyloxy-(4-chlorophenyl)]-3-hydroxypiperidine (150 mg) as a white powder. Mass spectrum (ES) [M+CH$_3$CN]$^+$=359.

Example 7

Resin-bound cis-[rac]-4,4-[benzyloxy-(4-chlorophenyl)]-3-hydroxypiperidine

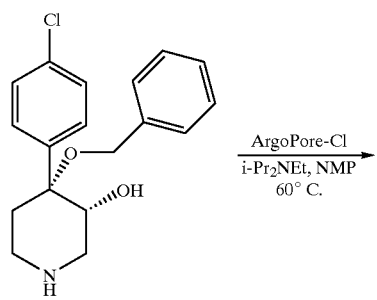

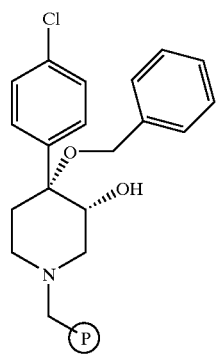

A mixture of cis-[rac]-4,4-[benzyloxy-(4-chlorophenyl)]-3-hydroxypiperidine (Example 6, 7.3 g, 23 mmol), ArgoPore-Cl resin (16 g, 15.3 mmol, loading capacity: 0.96 mmol from Argonaut Inc.), and N,N-diisopropylethylamine (13 mL, 76.7 mmol) in N-methylpyrrolinone (12 mL) was heated at 60° C. overnight. The resin was filtered and washed successively with CH$_2$Cl$_2$, and MeOH. The resin was dried at 40° C./high vacuum overnight to provide resin-bound 4,4-[benzyloxy-(4-chlorophenyl)]-3-hydroxypiperidine.

Example 8 cis-[rac]-4-Benzyloxy-4-(4-chloro-phenyl)-3-substituted piperidine library

General Procedure

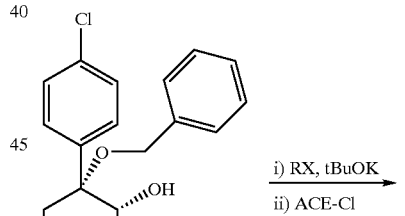

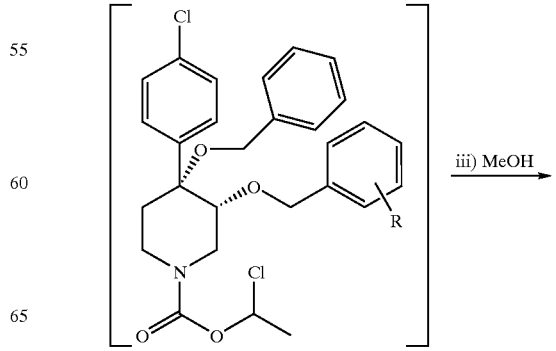

-continued

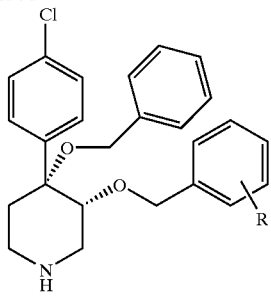

To a suspension of resin-bound cis-[rac]-4,4-[benzyloxy-(4-chlorophenyl)]-3-hydroxypiperidine (Example 7, 200 mg, 0.192 mmol, loading capacity: 0.96 mmol/g) and alkyl halide (RX, 0.58 mmol) in 4:1 THF:DMF solution (2 mL) was added potassium t-butoxide (0.77 M in THF; 1 mL, 0.77 mmol). After stirring at room temperature overnight, the resin was filtered and washed successively with N,N-dimethylformamide, tetrahydrofuran, methanol, dichloromethane, and diethyl ether. The resin was dried at 40° C./high vacuum overnight. 1-Chloroethyl chloroformate (0.2 mL, 1.9 mmol) was added to the resin in 1,2-dichloroethane (2 mL). After shaking 4 hours at room temperature, the resin was filtered off and washed with 1,2-dichloroethane (3×2 mL). The filtrate was evaporated in vacuo. Dry methanol (2 mL) was added to the residue and the solution was heated at 60° C. for 3 hours. The solution was evaporated in vacuo to provide the desired product.

In the manner described above, the following compounds were prepared.

| Example | Starting Material: Alkyl halide (RX) | Product | Nomenclature | Mass Spectrum (ES) |
|---|---|---|---|---|
| 8A | 3,4-DIFLUOROBENZYL BROMIDE (Aldrich) | Molecular Weight = 443.92 | 4-Benzyloxy-4-(4-chlorophenyl)-3-(3,4-difluorobenzyloxy)-piperidine | 444 |
| 8B | 2,6-DIFLUOROBENZYL BROMIDE (Aldrich) | Molecular Weight = 443.92 | 4-Benzyloxy-4-(4-chlorophenyl)-3-(2,6-difluorobenzyloxy)-piperidine | 444 |
| 8C | 2-PHENYLBENZYL BROMIDE (Aldrich) | Molecular Weight = 484.04 | 4-Benzyloxy-3-(biphenyl-2-ylmethoxy)-4-(4-chlorophenyl)-piperidine | 484 |

-continued

| Example | Starting Material: Alkyl halide (RX) | Product | Nomenclature | Mass Spectrum (ES) |
|---|---|---|---|---|
| 8D | ALPHA-BROMO-P-TOLUNITRILE (Aldrich) | 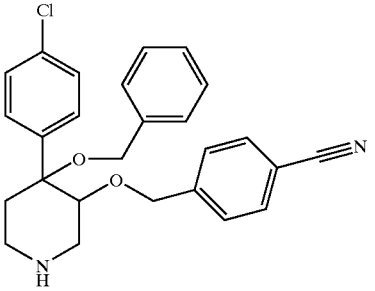 Molecular Weight = 432.95 | 4-[4-Benzyloxy-4-(4-chloro-phenyl)-piperidin-3-yloxymethyl]-benzonitrile | 433 |
| 8E | 3-NITROBENZYL BROMIDE (Lancaster) | 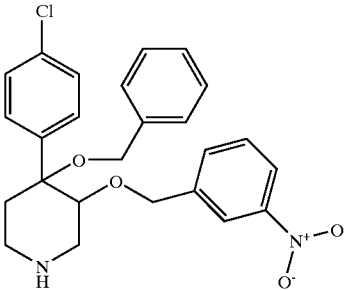 Molecular Weight = 452.94 | 4-[4-Benzyloxy-4-(4-chloro-phenyl)-3-(3-nitro-benzyloxy)-piperidine | 453 |
| 8F | 3-BROMOBENZYL BROMIDE (Aldrich) | 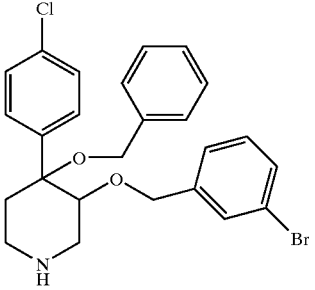 Molecular Weight = 486.83 | 4-Benzyloxy-3-(3-bromo-benzyloxy)-4-(4-chloro-phenyl)-piperidine | 487 |
| 8G | 2,4-DIFLUOROBENZYL BROMIDE (Lancaster) | 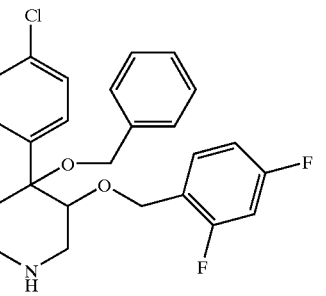 Molecular Weight = 443.92 | 4-Benzyloxy-4-(4-chloro-phenyl)-3-(2,4-difluoro-benzyloxy)-piperidine | 444 |

-continued

| Example | Starting Material: Alkyl halide (RX) | Product | Nomenclature | Mass Spectrum (ES) |
|---|---|---|---|---|
| 8H | 2-CHLORO-4-FLUOROBENZYL BROMIDE (Lancaster) | 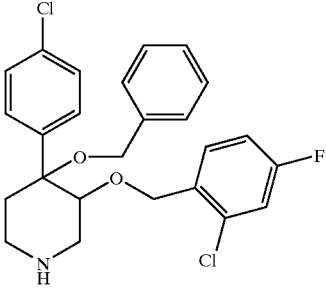 Molecular Weight = 460.37 | 4-Benzyloxy-3-(2-chloro-4-fluoro-benzyloxy)-4-(4-chloro-phenyl)-piperidine | 460 |
| 8I | METHYL 4-(BROMOMETHYL) BENZOATE (Aldrich) | 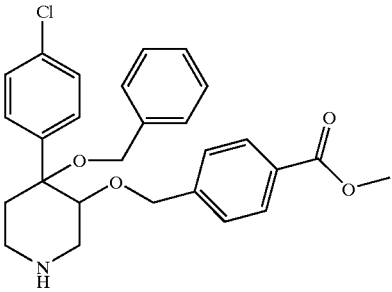 Molecular Weight = 465.97 | 4-[4-Benzyloxy-4-(4-chloro-phenyl)-piperidin-3-yloxymethyl]-benzoic acid methyl ester | 466 |
| 8J | 3,5-DIFLUOROBENZYL BROMIDE (Lancaster) | 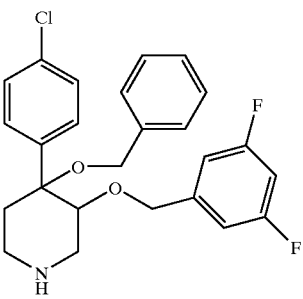 Molecular Weight = 443.92 | 4-Benzyloxy-4-(4-chloro-phenyl)-3-(3,5-difluoro-benzyloxy)-piperidine | 444 |
| 8K | 3-CHLORO-2-FLUOROBENZYL BROMIDE (Lancaster) | 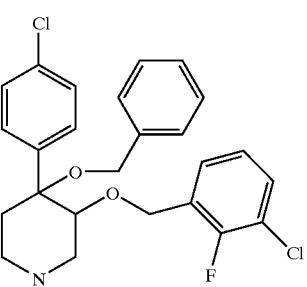 Molecular Weight = 460.37 | 4-Benzyloxy-3-(3-chloro-2-fluoro-benzyloxy)-4-(4-chloro-phenyl)-piperidine | 460 |

-continued

| Example | Starting Material: Alkyl halide (RX) | Product | Nomenclature | Mass Spectrum (ES) |
|---|---|---|---|---|
| 8L | 2,5-DICHLOROBENZYL BROMIDE (Lancaster) | Molecular Weight = 476.83 | 4-Benzyloxy-4-(4-chloro-phenyl)-3-(2,5-dichloro-benzyloxy)-piperidine | 477 |
| 8M | 2,3-DIFLUOROBENZYL BROMIDE (Aldrich) | Molecular Weight = 443.92 | 4-Benzyloxy-4-(4-chloro-phenyl)-3-(2,3-difluoro-benzyloxy)-piperidine | 444 |
| 8N | 4-(TRIFLUORO-METHYL)BENZYL BROMIDE (Aldrich) | Molecular Weight = 475.94 | 4-Benzyloxy-4-(4-chloro-phenyl)-3-(4-trifluoromethyl-benzyloxy)-piperidine | 476 |
| 8O | 4-FLUOROBENZYL BROMIDE (Aldrich) | Molecular Weight = 425.93 | 4-Benzyloxy-4-(4-chloro-phenyl)-3-(4-fluoro-benzyloxy)-piperidine | 426 |

-continued

| Example | Starting Material: Alkyl halide (RX) | Product | Nomenclature | Mass Spectrum (ES) |
|---|---|---|---|---|
| 8P | 4-BROMOBENZYL-BROMIDE (Aldrich) | 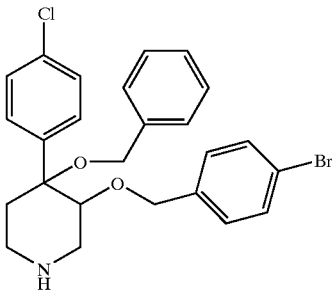 Molecular Weight = 486.83 | 4-Benzyloxy-3-(4-bromo-benzyloxy)-4-(4-chloro-phenyl)-piperidine | 487 |
| 8Q | 3-FLUOROBENZYL BROMIDE (Aldrich) | 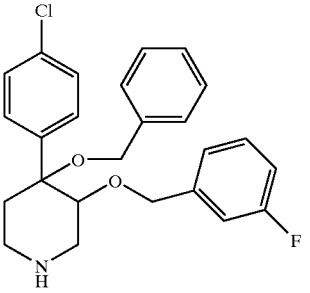 Molecular Weight = 425.93 | 4-Benzyloxy-4-(4-chloro-phenyl)-3-(3-fluoro-benzyloxy)-piperidine | 426 |
| 8R | ALPHA-BROMO-O-TOLUNITRILE (Aldrich) | 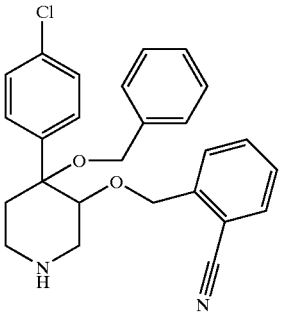 Molecular Weight = 432.95 | 2-[4-Benzyloxy-4-(4-chloro-phenyl)-piperidin-3-yloxymethyl]-benzonitrile | 433 |
| 8S | ALPHA-BROMO-M-TOLUNITRILE (Aldrich) | 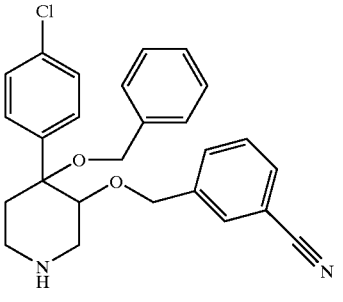 Molecular Weight = 432.95 | 3-[4-Benzyloxy-4-(4-chloro-phenyl)-piperidin-3-yloxymethyl]-benzonitrile | 433 |

-continued

| Example | Starting Material: Alkyl halide (RX) | Product | Nomenclature | Mass Spectrum (ES) |
|---|---|---|---|---|
| 8T | 4,5-DIMETHOXY-2-NITROBENZYL BROMIDE (Aldrich) | 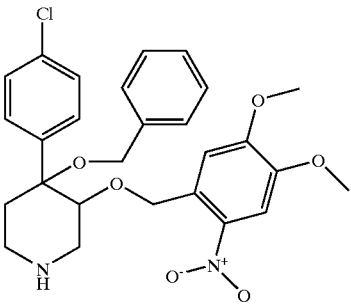 Molecular Weight = 512.99 | 4-Benzyloxy-4-(4-chloro-phenyl)-3-(4,5-dimethoxy-2-nitro-benzyloxy)-piperidine | 513 |
| 8U | CROTYL BROMIDE (Aldrich) | 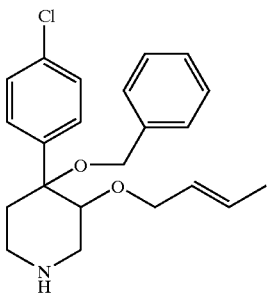 Molecular Weight = 371.91 | 4-Benzyloxy-3-but-2-enyloxy-4-(4-chloro-phenyl)-piperidine | 372 |
| 8V | 1-BROMO-2-PENTENE (Aldrich) | 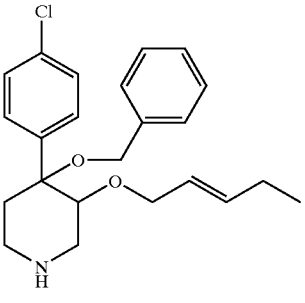 Molecular Weight = 385.93 | 4-Benzyloxy-4-(4-chloro-phenyl)-3-pent-2-enyloxy-piperidine | 386 |
| 8W | 2,3,6-TRIFLUORO-BENZYL BROMIDE (Aldrich) | 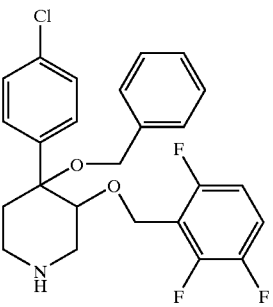 Molecular Weight = 461.91 | 4-Benzyloxy-4-(4-chloro-phenyl)-3-(2,3,6-trifluoro-benzyloxy)-piperidine | 462 |

-continued

| Example | Starting Material: Alkyl halide (RX) | Product | Nomenclature | Mass Spectrum (ES) |
|---------|--------------------------------------|---------|--------------|---------------------|
| 8X | 1-IODOBUTANE (Aldrich) | Molecular Weight = 373.92 | 4-Benzyloxy-3-butoxy-4-(4-chloro-phenyl)-piperidine | 374 |
| 8Y | 4-CHLORO-2-FLUOROBENZYL BROMIDE (Maybridge) | Molecular Weight = 460.37 | 4-Benzyloxy-3-(4-chloro-2-fluoro-benzyloxy)-4-(4-chloro-phenyl)-piperidine | 460 |
| 8Z | 4-BROMO-2-FLUOROBENZYL BROMIDE (Aldrich) | Molecular Weight = 504.82 | 4-Benzyloxy-3-(4-bromo-2-fluoro-benzyloxy)-4-(4-chloro-phenyl)-piperidine | 505 |
| 8Aa | 2,4,6-TRIFLUORO-BENZYL BROMIDE (Lancaster) | Molecular Weight = 461.91 | 4-Benzyloxy-4-(4-chloro-phenyl)-3-(2,4,6-trifluoro-benzyloxy)-piperidine | 462 |

-continued

| Example | Starting Material: Alkyl halide (RX) | Product | Nomenclature | Mass Spectrum (ES) |
|---|---|---|---|---|
| 8Ab | 2,4,5-TRIFLUORO-BENZYL BROMIDE (Lancaster) | Molecular Weight = 461.91 | 4-Benzyloxy-4-(4-chloro-phenyl)-3-(2,4,5-trifluoro-benzyloxy)-piperidine | 462 |
| 8Ac | 2,3,4-TRIFLUORO-BENZYL BROMIDE (Lancaster) | Molecular Weight = 461.91 | 4-Benzyloxy-4-(4-chloro-phenyl)-3-(2,3,4-trifluoro-benzyloxy)-piperidine | 462 |

Example 9 cis-[rac]-3-benzyloxy-4,4-[(4-chlorophenyl)-hydroxyl piperidine

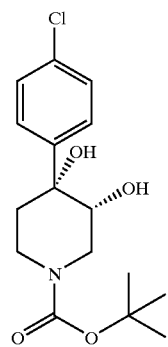

1. Benzyl bromide
   NaH, THF/DMF (4/1)
2. 50%, TFA/CH$_2$Cl$_2$

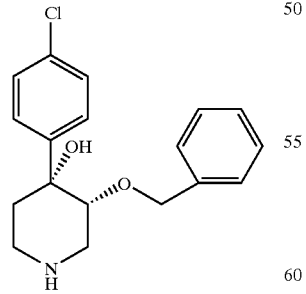

cis-[rac]-3-benzyloxy-4,4-[(4-chlorophenyl)-hydroxy]piperidine was prepared from cis-[rac]-4-(4-chlorophenyl)-3,4-dihydroxypiperidine-1-carboxylic acid tert-butyl ester (Example 1) and benzyl bromide (Aldrich) following the procedure used in Examples 2 and 6.

Example 10

Resin-bound cis-[rac]-3-benzyloxy-4,4-1(4-chlorophenyl)-hydroxy]piperidine

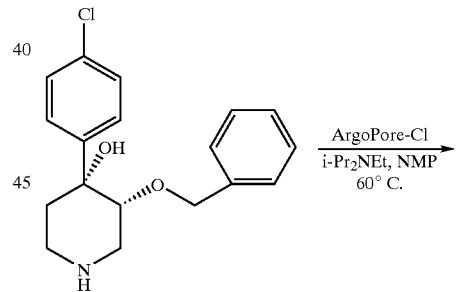

ArgoPore-Cl
i-Pr$_2$NEt, NMP
60° C.

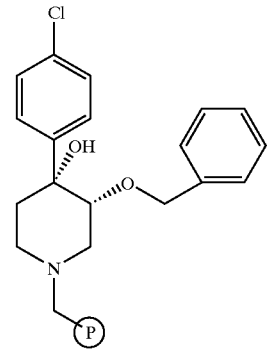

This resin-bound compound was prepared from cis-[rac]-3-benzyloxy-4,4-[(4-chlorophenyl)-hydroxy]piperidine (Example 9) following the procedure used in Example 7.

Example 11 cis-[rac]-3-Benzyloxy-4-(4-chlorophenyl)-4-substituted piperidine library

General Procedure

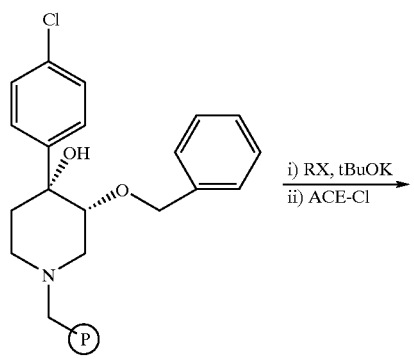

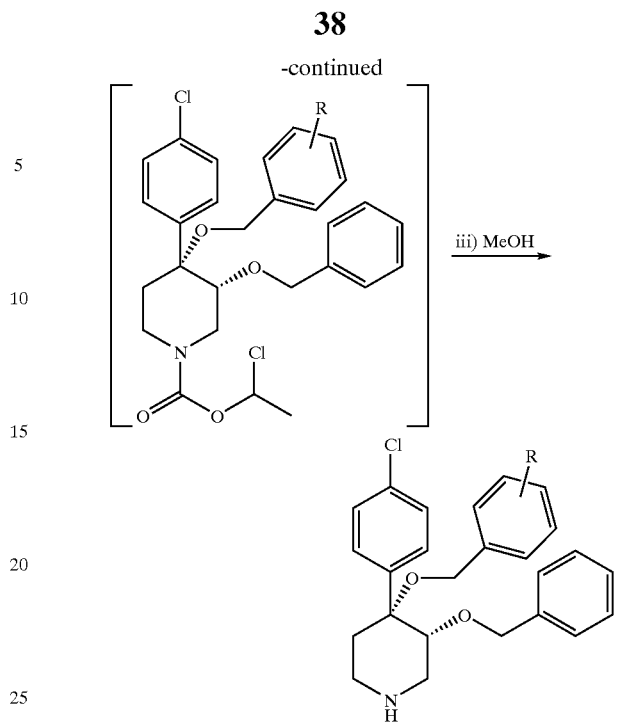

cis-[rac]-3-Benzyloxy-4-(4-chlorophenyl)-4-substituted piperidine was prepared from resin-bound cis-[rac]-3-benzyloxy-4,4-[(4-chlorophenyl)-hydroxy]piperidine (Example 10) and alkyl bromide following the procedure used in Example 8.

In the manner described above, the following compounds were prepared.

| Example | Starting Material: Alkyl halide (RX) | Product | Nomenclature | Mass Spectrum (ES) |
|---|---|---|---|---|
| 11A | 2,4,6-TRIFLUORO BENZYL BROMIDE (Lancaster) | 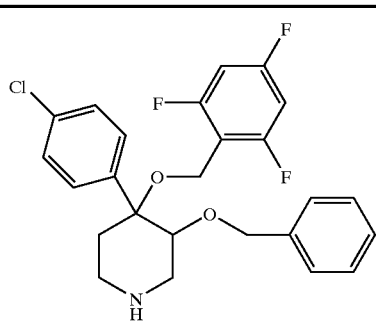 Molecular Weight = 461.91 | 3-Benzyloxy-4-(4-chlorophenyl)-4-(2,4,6-trifluorobenzyloxy)-piperidine | 462 |
| 11B | 2,5-DICHLOROBENZYL BROMIDE (Lancaster) | 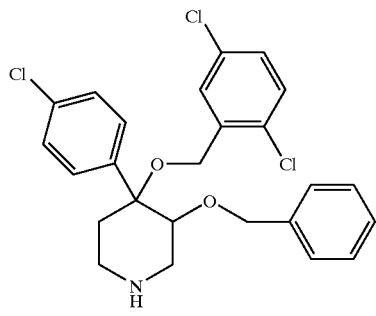 Molecular Weight = 476.83 | 3-Benzyloxy-4-(4-chlorophenyl)-4-(2,5-dichlorobenzyloxy)-piperidine | 477 |

| Example | Starting Material: Alkyl halide (RX) | Product | Nomenclature | Mass Spectrum (ES) |
|---|---|---|---|---|
| 11C | 2,6-DICHLOROBENZYL BROMIDE (Aldrich) | 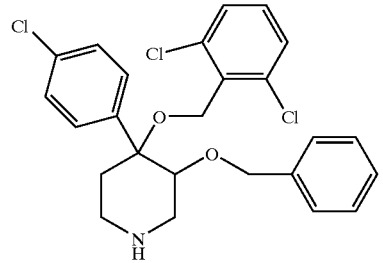 Molecular Weight = 476.83 | 3-Benzyloxy-4-(4-chloro-phenyl)-4-(2,6-dichloro-benzyloxy)-piperidine | 477 |
| 11D | 2,6-DIFLUOROBENZYL BROMIDE (Aldrich) | 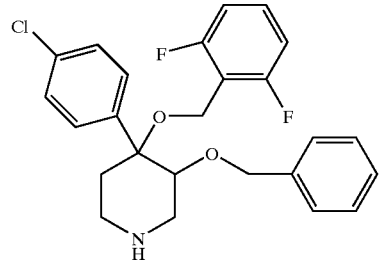 Molecular Weight = 443.92 | 3-Benzyloxy-4-(4-chloro-phenyl)-4-(2,6-difluoro-benzyloxy)-piperidine | 444 |
| 11E | 3-METHOXYBENZYL BROMIDE (Aldrich) | 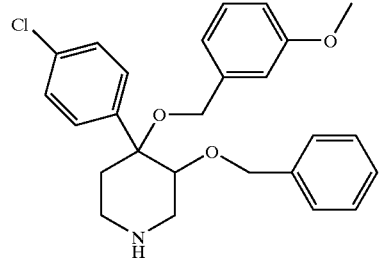 Molecular Weight = 437.96 | 3-Benzyloxy-4-(4-chloro-phenyl)-4-(3-methoxy-benzyloxy)-piperidine | 438 |
| 11F | 2,3,6-TRIFLUORO BENZYL BROMIDE (Aldrich) | 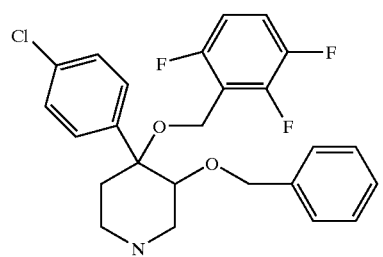 Molecular Weight = 461.91 | 3-Benzyloxy-4-(4-chloro-phenyl)-4-(2,3,6-trifluoro-benzyloxy)-piperidine | 462 |

| Example | Starting Material: Alkyl halide (RX) | Product | Nomenclature | Mass Spectrum (ES) |
|---|---|---|---|---|
| 11G | 2-FLUOROBENZYL BROMIDE (Aldrich) | 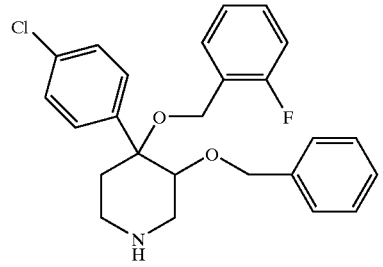 Molecular Weight = 425.93 | 3-Benzyloxy-4-(4-chloro-phenyl)-4-(2-fluoro-benzyloxy)-piperidine | 426 |
| 11H | 2-FLUORO-3-METHYLBENZYL BROMIDE (Maybridge) | 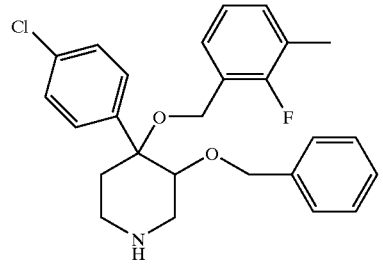 Molecular Weight = 439.96 | 3-Benzyloxy-4-(4-chloro-phenyl)-4-(2-fluoro-3-methyl-benzyloxy)-piperidine | 440 |

Example 12

Resin-bound 3-(3,4-dichlorobenzyloxy)-4,4-[(4-chlorophenyl)-hydroxy]piperidine

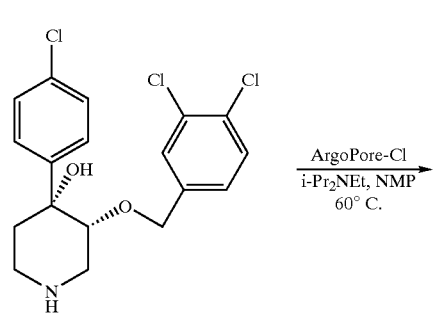

This resin-bound compound was prepared following the procedure used in Examples 2, 6, and 7.

Example 13

4-(4-Chloro-phenyl)-3-(3,4-dichloro-benzyloxy)-4-substituted piperidine

General Procedure

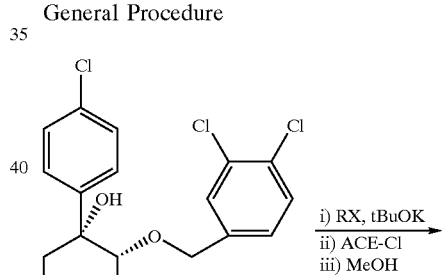

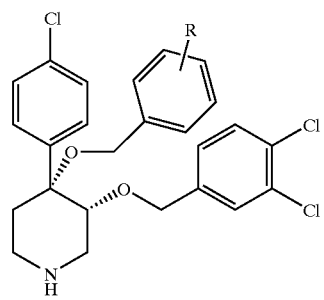

4-(4-Chloro-phenyl)-3-(3,4-dichloro-benzyloxy)-4-substituted piperidine was prepared from resin-bound 3-(3,4-dichlorobenzyloxy)-4,4-[(4-chlorophenyl)-hydroxy]

piperidine (Example 12) and alkyl bromide following the procedure used in Example 8.

In the manner described above, the following compounds were prepared.

| Example | Starting Material: Alkyl halide (RX) | Product | Nomenclature | Mass Spectrum (ES) |
|---|---|---|---|---|
| 13A | 4-FLUOROBENZYL BROMIDE (Aldrich) | Molecular Weight = 494.82 | 4-(4-Chloro-phenyl)-3-(3,4-dichloro-benzyloxy)-4-(4-fluoro-benzyloxy)-piperidme | 496 |
| 13B | 4-BROMOBENZYL BROMIDE (Aldrich) | Molecular Weight = 555.72 | 4-(4-Bromo-benzyloxy)-4-(4-chloro-phenyl)-3-(3,4-dichloro-benzyloxy)-piperidine | 556 |
| 13C | 2,4-DIFLUOROBENZYL BROMIDE (Lancaster) | Molecular Weight = 512.81 | 4-(4-Chloro-phenyl)-3-(3,4-dichloro-benzyloxy)-4-(2,4-difluoro-benzyloxy)-piperidine | 514 |

-continued

| Example | Starting Material: Alkyl halide (RX) | Product | Nomenclature | Mass Spectrum (ES) |
|---|---|---|---|---|
| 13D | 2-CHLORO-4-FLUOROBENZYLBROMIDE (Lancaster) | Molecular Weight = 529.26 | 4-(2-Chloro-4-fluoro-benzyloxy)-4-(4-chloro-phenyl)-3-(3,4-dichloro-benzyloxy)-piperidine | 530 |
| 13E | 2-BROMOBENZYL BROMIDE (Aldrich) | Molecular Weight = 555.72 | 4-(2-Bromo-benzyloxy)-4-(4-chloro-phenyl)-3-(3,4-dichloro-benzyloxy)-piperidine | 556 |
| 13F | 4-(TERT-BUTYL)BENZYL BROMIDE (Fluka) | Molecular Weight = 532.94 | 4-(4-tert-Butyl-benzyloxy)-4-(4-chloro-phenyl)-3-(3,4-dichloro-benzyloxy)-piperidine | 533 |
| 13G | ALPHA-BROMO-P-TOLUNITRILE (Aldrich) | Molecular Weight = 501.84 | 4-[4-(4-Chloro-phenyl)-3-(3,4-dichloro-benzyloxy)-piperidin-4-yloxymethyl]-benzonitrile | 502 |

| Example | Starting Material: Alkyl halide (RX) | Product | Nomenclature | Mass Spectrum (ES) |
|---|---|---|---|---|
| 13H | 3-CHLOROBENZYL BROMIDE (Aldrich) | 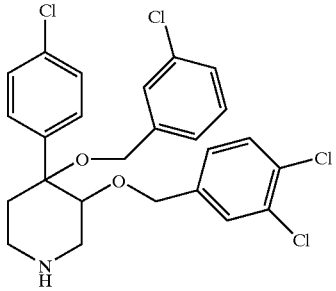 Molecular Weight = 511.27 | 4-(3-Chloro-benzyloxy)-4-(4-chloro-phenyl)-3-(3,4-dichloro-benzyloxy)-piperidine | 512 |
| 13I | 3-BROMOBENZYL BROMIDE (Aldrich) | 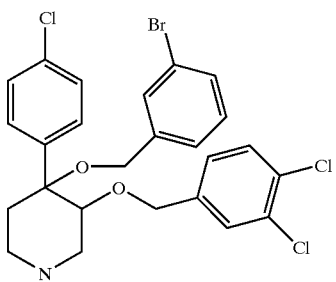 Molecular Weight = 555.72 | 4-(3-Bromo-benzyloxy)-4-(4-chloro-phenyl)-3-(3,4-dichloro-benzyloxy)-piperidine | 556 |
| 13J | 2-FLUOROBENZYL BROMIDE (Aldrich) | 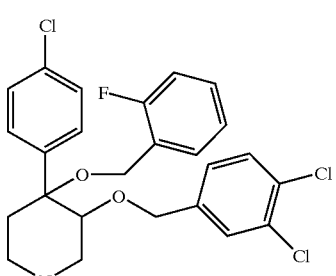 Molecular Weight = 494.82 | 4-(4-Chloro-phenyl)-3-(3,4-dichloro-benzyloxy)-4-(2-fluoro-benzyloxy)-piperidine | 496 |
| 13K | 3,5-DIFLUOROBENZYL BROMIDE (Lancaster) | 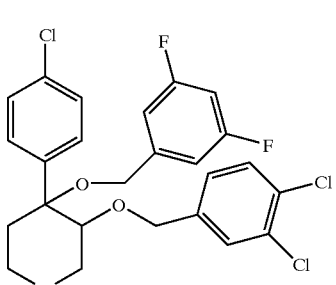 Molecular Weight = 512.81 | 4-(4-Chloro-phenyl)-3-(3,4-dichloro-benzyloxy)-4-(3,5-difluoro-benzyloxy)-piperidine | 514 |

-continued

| Example | Starting Material: Alkyl halide (RX) | Product | Nomenclature | Mass Spectrum (ES) |
|---|---|---|---|---|
| 13L | 3-CHLORO-2-FLUOROBENZYL BROMIDE (Lancaster) | 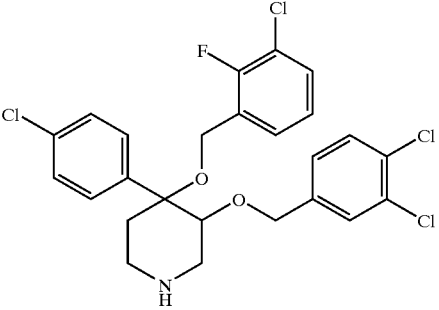 Molecular Weight = 529.26 | 4-(3-Chloro-2-fluoro-benzyloxy)-4-(4-chloro-phenyl)-3-(3,4-dichloro-benzyloxy)-piperidine | 530 |
| 13M | 2,3-DIFLUOROBENZYL BROMIDE (Aldrich) | 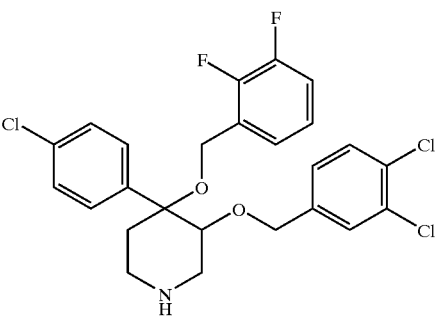 Molecular Weight = 512.81 | 4-(4-Chloro-phenyl)-3-(3,4-dichloro-benzyloxy)-4-(2,3-difluoro-benzyloxy)-piperidine | 514 |
| 13N | 4-(TRIFLUORO-METHYL)BENZYL BROMIDE (Aldrich) | 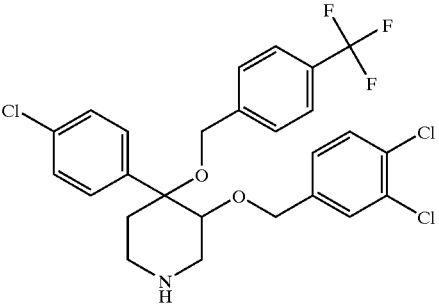 Molecular Weight = 544.83 | 4-(4-Chloro-phenyl)-3-(3,4-dichloro-benzyloxy)-4-(4-trifluoromethyl-benzyloxy)-piperidine | 546 |
| 13O | 3-FLUOROBENZYL BROMIDE (Aldrich) | 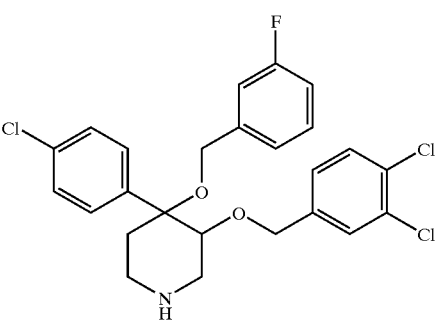 Molecular Weight = 494.82 | 4-(4-Chloro-phenyl)-3-(3,4-dichloro-benzyloxy)-4-(3-fluoro-benzyloxy)-piperidine | 496 |

-continued

| Example | Starting Material: Alkyl halide (RX) | Product | Nomenclature | Mass Spectrum (ES) |
|---|---|---|---|---|
| 13P | ALPHA-BROMO-M-TOLUNITRILE (Aldrich) | 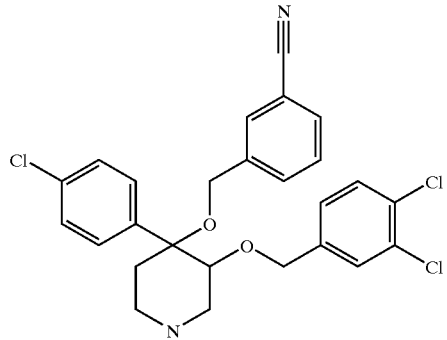 Molecular Weight = 501.84 | 3-[4-(4-Chloro-phenyl)-3-(3,4-dichloro-benzyloxy)-piperidin-4-yloxymethyl]-benzonitrile | 503 |
| 13Q | 2-CHLOROBENZYL BROMIDE (Aldrich) | 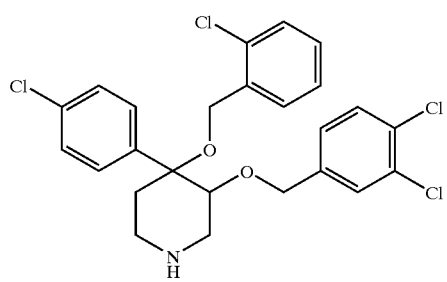 Molecular Weight = 511.27 | 4-(2-Chloro-benzyloxy)-4-(4-chloro-phenyl)-3-(3,4-dichloro-benzyloxy)-piperidine | 512 |
| 13R | 4-METHYLBENZYL BROMIDE (Fluka) | 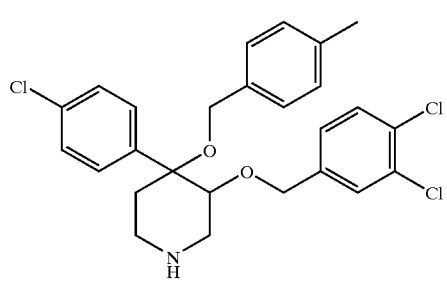 Molecular Weight = 490.86 | 4-(4-Chloro-phenyl)-3-(3,4-dichloro-benzyloxy)-4-(4-methyl-benzyloxy)-piperidine | 492 |

Example 14

Resin-bound cis-[rac]-4-(4-Chloro-phenyl)-piperidine-3,4-diol

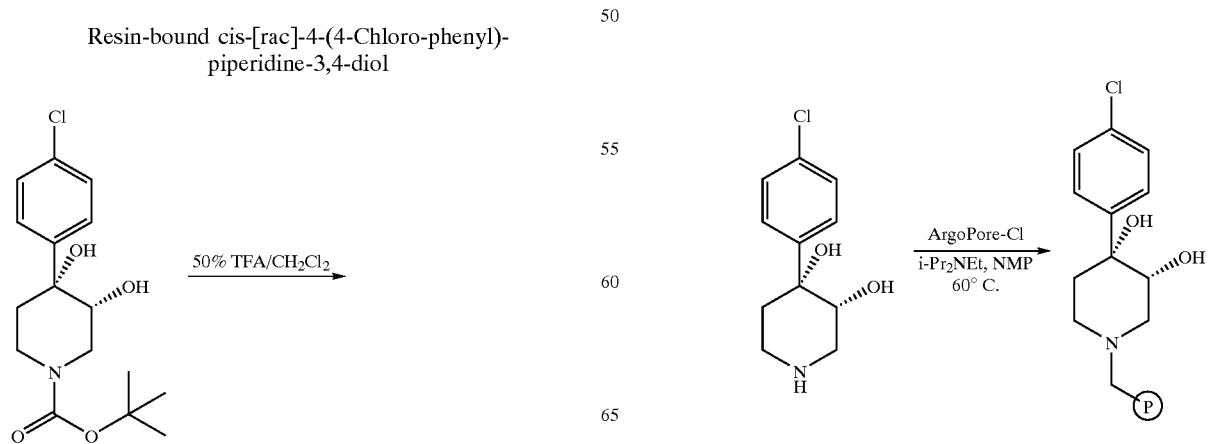

This resin-bound compound was prepared from cis-[rac]-4-(4-chlorophenyl)-3,4-dihydroxypiperidine-1-carboxylic acid tert-butyl ester (Example 1) following the procedure used in Example 6 and 7.

Example 15 cis-[rac]-4-(4-Chloro-phenyl)-3,4-bis-(2,4-difluoro-benzyloxy)-piperidine

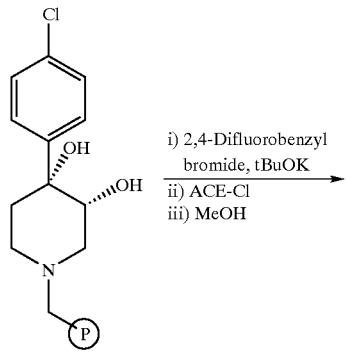

i) 2,4-Difluorobenzyl bromide, tBuOK
ii) ACE-Cl
iii) MeOH

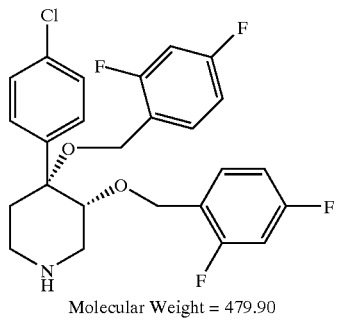

Molecular Weight = 479.90

To a suspension of resin-bound 4-(4-Chloro-phenyl)-piperidine-3,4-diol (Example 14, 200 mg, 0.192 mmol, loading capacity: 0.96 mmol/g) and 2,4-difluorobenzyl bromide (Lancaster, 1.54 mmol) in 4:1 THF:DMF solution (2 mL) was added potassium t-butoxide (0.77 M in THF; 1 mL, 0.77 mmol). After stirring at room temperature overnight, the resin was filtered and washed successively with N,N-dimethylformamide, tetrahydrofuran, methanol, dichloromethane, and diethyl ether. The resin was dried at 40° C./high vacuum overnight. 1-Chloroethyl chloroformate (0.2 mL, 1.9 mmol) was added to the resin in 1,2-dichloroethane (2 mL). After shaking 4 hours at room temperature, the resin was filtered off and washed with 1,2-dichloroethane (3×2 mL). The filtrate was evaporated in vacuo. Dry methanol (2 mL) was added to the residue and the solution was heated at 60° C. for 3 hours. The solution was evaporated in vacuo to provide the desired product. Mass spectrum (ES) M$^+$=480.

Example 16 cis-[rac]-4-(4-Chloro-phenyl)-3,4-bis-(3-nitro-benzyloxy)-piperidine

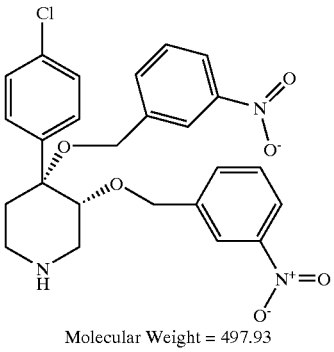

Molecular Weight = 497.93 cis-[rac]-4-(4-Chloro-phenyl)-3,4-bis-(3-nitro-benzyloxy)-piperidine was prepared from resin-bound 4-(4-Chloro-phenyl)-piperidine-3,4-diol (Example 14) and 3-nitrobenzyl bromide (Lancaster) following the procedure used in Example 15. Mass spectrum (ES) M$^+$=498.

Example 17 cis-[rac]-1-[4-Benzyloxy-4-(4-chloro-phenyl)-3-substituted-piperidin-1-yl]-ethanone library
General Procedure

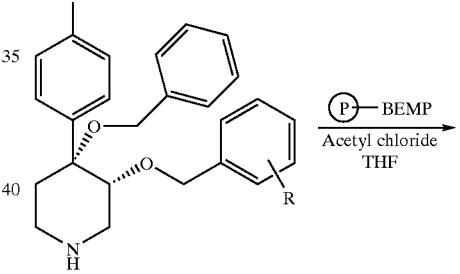

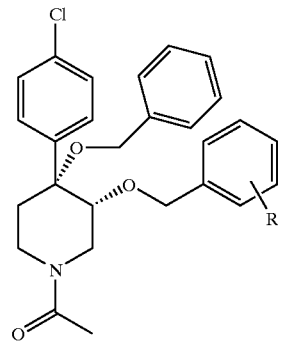

A mixture of 4,4-[benzyloxy-(4-chlorophenyl)]-3-aryloxypiperidine (Example 8, 0.012 mmol), polymer-supported BEMP (10 mg, 0.023 mmol, loading capacity: 2.3 mmol/g from Fluka Inc.), and acetyl chloride (0.01 mL, 0.14 mmol) in tetrahydrofuran (1 mL) was shaken at room temperature overnight. The resin was filtered and washed successively with CH$_2$Cl$_2$, and MeOH. The filtrate was evaporated in vacuo to provide the desired product.

In the manner described above, the following compounds were prepared.

| Example | Starting Material | Product | Nomenclature | Mass Spectrum (ES) |
|---|---|---|---|---|
| 17A | Example 8G | Molecular Weight = 485.96 | 1-[4-Benzyloxy-4-(4-chloro-phenyl)-3-(2,4-difluoro-benzyloxy)-piperidin-1-yl]-ethanone | 486 |
| 17B | Example 8F | Molecular Weight = 528.87 | 1-[4-Benzyloxy-3-(3-bromo-benzyloxy)-4-(4-chloro-phenyl)-piperidin-1-yl]-ethanone | 530 |
| 17C | Example 8H | Molecular Weight = 502.41 | 1-[4-Benzyloxy-3-(2-chloro-4-fluoro-benzyloxy)-4-(4-chloro-phenyl)-piperidin-1-yl]-ethanone | 502 |
| 17D | Example 8D | Molecular Weight = 485.96 | 1-[4-Benzyloxy-4-(4-chloro-phenyl)-3-(3,5-difluoro-benzyloxy)-piperidin-1-yl]-ethanone | 486 |

| Example | Starting Material | Nomenclature | Mass Spectrum (ES) |
|---|---|---|---|
| 17E | Example 8K | 1-[4-Benzyloxy-3-(3-chloro-2-fluoro-benzyloxy)-4-(4-chloro-phenyl)-piperidin-1-yl]-ethanone<br>Molecular Weight = 502.41 | 502 |
| 17F | Example 4 | 1-[4-Benzyloxy-4-(4-chloro-phenyl)-3-(3,4-dichloro-benzyloxy)-piperidin-1-yl]-ethanone<br>Molecular Weight = 518.87 | 518 |
| 17G | Example 8O | 1-[4-Benzyloxy-4-(4-chloro-phenyl)-3-(4-fluoro-benzyloxy)-piperidin-1-yl]-ethanone<br>Molecular Weight = 467.97 | 468 |
| 17H | Example 8P | 1-[4-Benzyloxy-3-(4-bromo-benzyloxy)-4-(4-chloro-phenyl)-piperidin-1-yl]-ethanone<br>Molecular Weight = 528.87 | 530 |

-continued

| Example | Starting Material | Product | Nomenclature | Mass Spectrum (ES) |
|---|---|---|---|---|
| 17I | Example 8Q | Molecular Weight = 467.97 | 1-[4-Benzyloxy-4-(4-chloro-phenyl)-3-(3-fluoro-benzyloxy)-piperidin-1-yl]-ethanone | 468 |
| 17J | Example 8S | Molecular Weight = 474.99 | 3-[1-Acetyl-4-benzyloxy-4-(4-chloro-phenyl)-piperidin-3-yloxymethyl]-benzonitrile | 475 |
| 17K | Example 8B | Molecular Weight = 485.96 | 1-[4-Benzyloxy-4-(4-chloro-phenyl)-3-(2,6-difluoro-benzyloxy)-piperidin-1-yl]-ethanone | 486 |
| 17L | Example 8E | Molecular Weight = 494.97 | 1-[4-Benzyloxy-4-(4-chloro-phenyl)-3-(3-nitro-benzyloxy)-piperidin-1-yl]-ethanone | 495 |

-continued

| Example | Starting Material | Product | Nomenclature | Mass Spectrum (ES) |
|---|---|---|---|---|
| 17M | Example 8Ac | Molecular Weight = 503.95 | 1-[4-Benzyloxy-4-(4-chloro-phenyl)-3-(2,3,4-trifluoro-benzyloxy)-piperidin-1-yl]-ethanone | 504 |
| 17N | Example 13J | Molecular Weight = 536.86 | 1-[4-(4-Chloro-phenyl)-3-(3,4-dichloro-benzyloxy)-4-(2-fluoro-benzyloxy)-piperidin-1-yl]-ethanone | 538 |

Example 18 cis-[rac]-1-[4-Benzyloxy-4-(4-chloro-phenyl)-3-(2,3,4-trifluoro-benzyloxy)-piperidin-1-yl]-propan-1-one

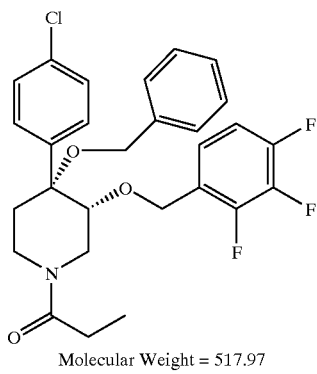

Molecular Weight = 517.97 cis-[rac]-1-[4-Benzyloxy-4-(4-chloro-phenyl)-3-(2,3,4-trifluoro-benzyloxy)-piperidin-1-yl]-propan-1-one was prepared from 4-Benzyloxy-4-(4-chloro-phenyl)-3-(2,3,4-trifluoro-benzyloxy)-piperidine (Example 8Ad) and propionyl chloride (Aldrich) following the procedure used in Example 17. Mass spectrum (ES) M$^+$=518.

Example 19 cis-[rac]-1-[4-Benzyloxy-4-(4-chloro-phenyl)-3-(3,4-dichloro-benzyloxy)-piperidin-1-yl]-propan-1-one

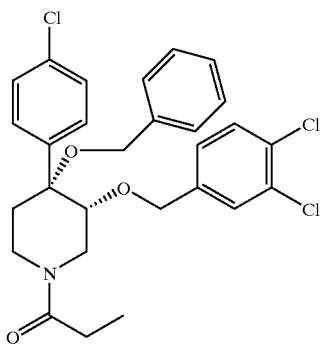

Molecular Weight = 532.89 cis-[rac]-1-[4-Benzyloxy-4-(4-chloro-phenyl)-3-(3,4-dichloro-benzyloxy)-piperidin-1-yl]-propan-1-one was prepared from cis-[rac]-4-(benzyloxy)-4-(4-chlorophenyl)-3-(3,4-dichlorobenzyloxy)-piperidine(Example 4) following the procedure used in Example 18. Mass spectrum (ES) M$^+$=533.

Example 20

Resin-bound cis-[rac]-4-benzyloxy-4-(4-fluoro-phenyl)-piperidin-3-ol

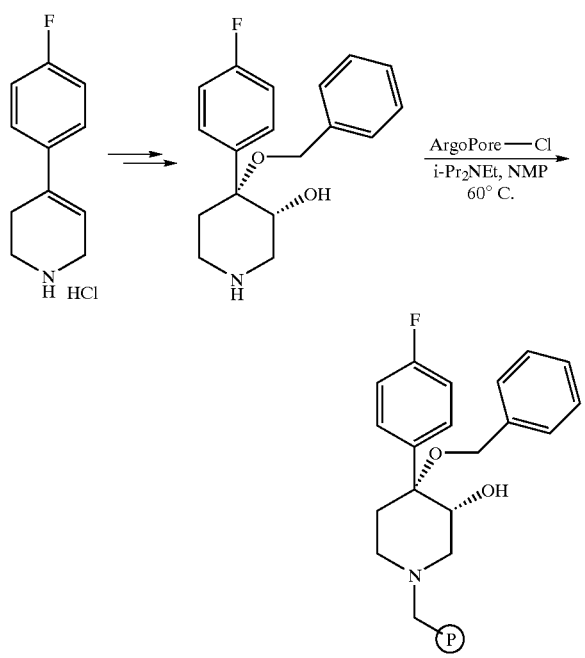

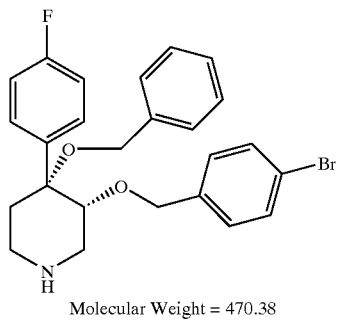

This resin-bound compound was prepared from 4-(4-fluorophenyl)-1,2,3,6-tetrahydropyridine hydrochloride (Acros) following the procedure used in Examples 1, 5, 6, and 7.

Example 21 cis-[rac]-4-Benzyloxy-3-(4-bromo-benzyloxy)-4-(4-fluoro-phenyl)-piperidine

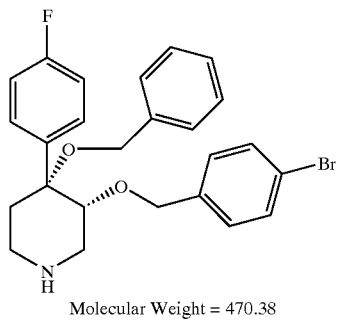

Molecular Weight = 470.38 cis-[rac]-4-Benzyloxy-3-(4-bromo-benzyloxy)-4-(4-fluoro-phenyl)-piperidine was prepared from resin-bound cis-[rac]-4-benzyloxy-4-(4-fluoro-phenyl)-piperidin-3-ol (Example 20) and 4-bromobenzyl bromide (Aldrich) following the procedure used in Example 8. Mass spectrum (ES) MH$^+$=471.

Example 22 cis-[rac]-4-Benzyloxy-4-(4-fluoro-phenyl)-3-pentyloxy-piperidine

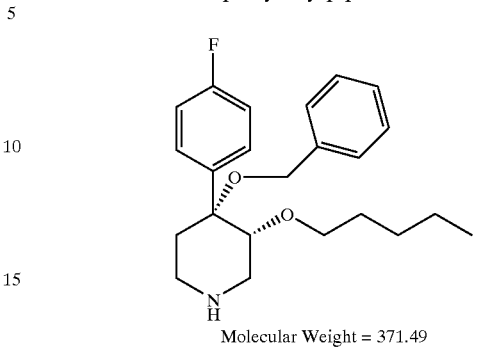

Molecular Weight = 371.49 cis-[rac]-4-Benzyloxy-4-(4-fluoro-phenyl)-3-pentyloxy-piperidine was prepared from resin-bound cis-[rac]-4-benzyloxy-4-(4-fluoro-phenyl)-piperidin-3-ol (Example 20) and 1-iodopentane (Aldrich) following the procedure used in Example 8. Mass spectrum (ES) MH$^+$=372.

Example 23 cis-[rac]-4-Benzyloxy-4-(4-chloro-phenyl)-3-(3,4-dichloro-benzyloxy)-1-ethyl-piperidine

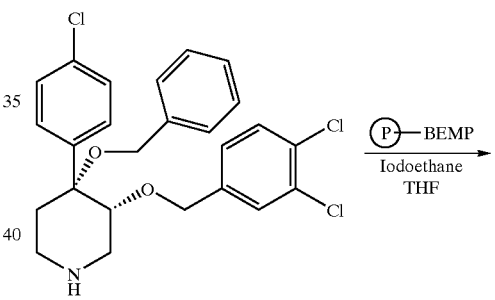

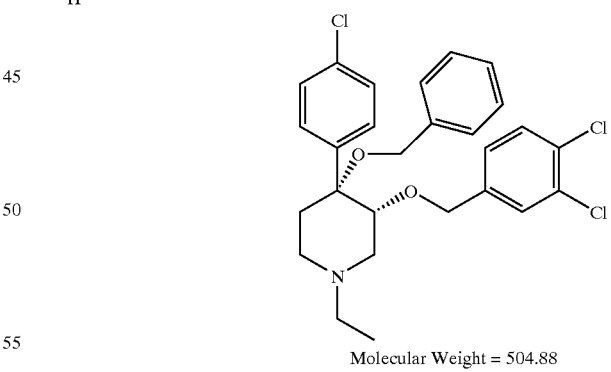

Molecular Weight = 504.88

A mixture of 4-benzyloxy-4-(4-chloro-phenyl)-3-(3,4-dichloro-benzyloxy)-piperidine (Example 4, 0.01 mmol), polymer-supported BBMP (6.5 mg, 0.015 mmol, loading capacity: 2.3 mmol/g from Fluka Inc.), iodoethane (Aldrich, 0.015 mmol) in tetrahydrofuran (1 mL) was shaken at room temperature overnight. The resin was filtered and washed successively with CH$_2$Cl$_2$, and MeOH. The filtrate was evaporated in vacuo to provide the desired product. Mass spectrum (ES) MH$^+$=506.

Example 24 cis-[rac]-4-Benzyloxy-4-(4-chloro-phenyl)-3-(3,4-dichloro-benloxy)-1-propyl-piperidine

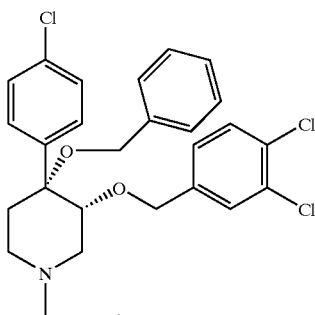

Molecular Weight = 518.91 cis-[rac]-4-Benzyloxy-4-(4-chloro-phenyl)-3-(3,4-dichloro-benzyloxy)-1-propyl-piperidine was prepared from 4-benzyloxy-4-(4-chloro-phenyl)-3-(3,4-dichloro-benzyloxy)-piperidine (Example 4) and 1-iodopropane (Aldrich) following the procedure used in Example 23. Mass spectrum (ES) M$^+$=519.

Example 25 cis-[rac]-3-[4-Benzyloxy-4-(4-chloro-phenyl)-3-(2,3,4-trifluoro-benzyloxy)-piperidin-1-yl]-propane-1,2-diol

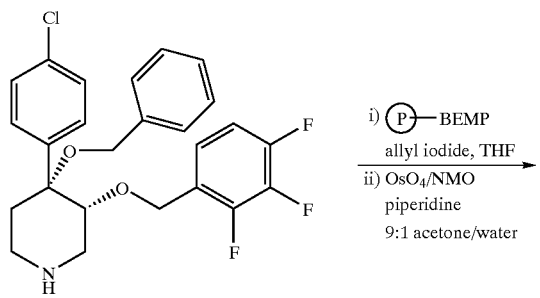

Molecular Weight = 535.99

A mixture of 4-benzyloxy-4-(4-chloro-phenyl)-3-(2,3,4-trifluoro-benzyloxy)-piperidine (Example 8Ac, 6 mg, 0.013 mmol), polymer-supported BEMP (10 mg, 0.023 mmol, loading capacity: 2.3 mmol/g from Fluka Inc.), allyl iodide (Aldrich, 3 uL, 0.003 mmol) in tetrahydrofuran (1 mL) was shaken at room temperature for 2 hours. The resin was filtered and washed successively with CH$_2$Cl$_2$, and MeOH. The filtrate was evaporated in vacuo. Without purification, the residue was dissolved in 9:1 acetone/water solution (1 mL). To the solution was added osmium tetroxide (Aldrich, 10 µL, 0.008 mmol) and 4-methylmorpholine N-oxide (Aldrich, 12 mg, 0.1 mmol). The mixture was stirred overnight and Na$_2$SO$_3$ was added. After stirring for 2 hours, the mixture was filtered through a silica gel pad. The filtrate was evaporated in vacuo to provide the desired product. Mass spectrum (ES) M$^+$=536.

Example 26 cis-[rac]-3-[4-Benzyloxy-3-(4-bromo-benzyloxy)-4-(4-chloro-phenyl)-piperidin-1-yl]-propane-1,2-diol

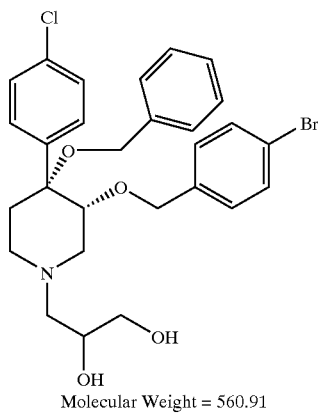

Molecular Weight = 560.91

This compound was prepared from 4-benzyloxy-3-(4-bromo-benzyloxy)-4-(4-chloro-phenyl)-piperidine (Example 8P) followed the procedure used in Example 25. Mass spectrum (ES) MH$^+$=562.

Example 27 cis-[rac]-3-[4-Benzyloxy-4-(4-chloro-phenyl)-3-(2,3,4-trifluoro-benzyloxy)-piperidin-1-yl]-methane sulfonyl

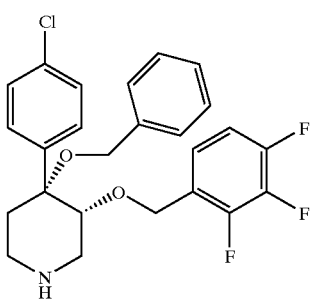

-continued

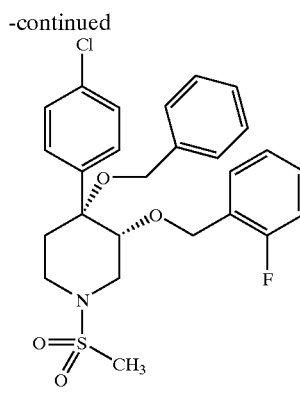

Molecular Weight = 540.00

To a solution of 4-benzyloxy-4-(4-chloro-phenyl)-3-(2,3,4-trifluoro-benzyloxy)-piperidine (Example 8Ac, 4 mg, 0.008 mmol) and triethylamine (6 uL, 0.08 mmol) in dichloromethane (0.5 mL) at 0° C. was added dropwise methanesulfonyl chloride (Aldrich, 2.5 uL, 0.015 mmol). After stirring for 2 hours, the mixture was filtered through an amino silica gel pad (Silicycle). The filtrate was evaporated in vacuo to provide the desired product. Mass spectrum (ES) MH$^+$=541.

Example 28
In Vitro Activity Assay

The ability of the substituted piperidine compounds of the invention to inhibit the interaction between p53 and MDM2 proteins was measured by an ELISA (Enzyme-Linked Immuno Sorbent Assay) in which recombinant GST-tagged MDM2 binds to a peptide that resembles the MDM2-interacting region of p53 (Böttger et al., J. Mol. Bio. 1997, Vol. 269, pgs. 744–756). This peptide is immobilized to the surface of a 96 well plate via N-terminal biotin, which binds to streptavidin-coated wells. MDM2 is added to each well in the presence of anti-MDM2 mouse monoclonal antibody (SMP-14, Santa Cruz Biotech). After removal of the unbound MDM2 protein, a peroxydase-linked secondary antibody (anti-mouse IgG, Roche Molecular Biochemicals) and the amount of peptide-bound MDM2 is determined calorimetrically by the addition of a peroxydase substrate (MTB Microwell Peroxydase Substrate System, Kirkegaard & Perry Labs).

Test plates were prepared by coating with streptavidin (5 mg/ml in PBS) for 2 hours followed by a PBS (phosphate-buffered saline) wash and overnight blocking with 150 μl of blocking buffer containing 2 mg/ml bovine serum albumin (Sigma) and 0.05% Tween 20 (Sigma) in PBS at 4° C. Biotinylated peptide (1 μM) is added to each well in 50 μl of blocking buffer and washed extensively after a 1-hour incubation. Test compounds were diluted in a separate 96 well plate and added in triplicate to a compound incubation plate containing a mix of the MDM2 protein and anti-MDM2 antibody. After 20 minutes incubation, the content of the plate is transferred to the test plate and incubated for an additional 1 hour. The secondary anti-mouse IgG antibody is added to the test plate preceded and followed by a triple wash with 0.05% Tween 20 in PBS. Finally, peroxydase substrate is added to each well and the absorption was read using a plate reader (MR$_{7000}$, Dynatech) at 450 nm. The inhibitory activity of the test compounds was measured as a percentage of the bound MDM2 in treated vs. untreated wells and IC$_{50}$ was calculated.

The inhibitory activity (IC$_{50}$) of the compounds prepared in the examples above, and represented by formula (I) or (II), is in the range of 3 μM to 100 μM.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

What is claimed is:

1. A compound represented by formula (I):

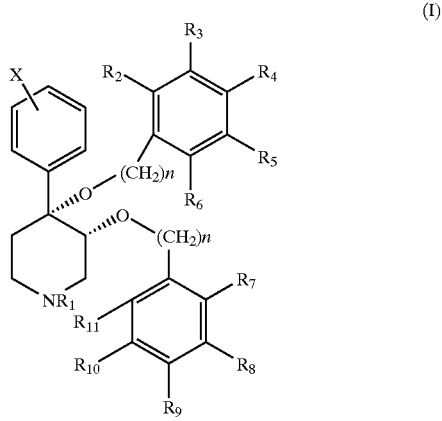

(I)

wherein
n is an integer independently selected from 1 or 2;
X is halogen;
R$_1$ is selected from the group consisting of hydrogen, carbonyl, sulfonyl, lower alkyl, and lower alkyl substituted by carbonyl, sulfonyl, or hydroxy;
R$_2$–R$_6$ are independently selected from the group consisting of hydrogen, halogen, lower alkyl, —C(CH$_3$)$_3$, CF$_3$, —OCH$_3$, —NO$_2$, and —CN; and
R$_7$–R$_{11}$ are independently selected from the group consisting of hydrogen, halogen, —CN, —NO$_2$, CF$_3$, —OCH$_3$, —COOCH$_3$, and —C$_6$H$_5$;
or a pharmaceutically acceptable salt thereof.

2. The compound of claim 1, wherein n is 1.
3. The compound of claim 1, wherein X is chloro.
4. The compound of claim 1, wherein X is a para substituent.
5. The compound of claim 1, wherein R$_1$ is selected from the group consisting of hydrogen, —CH$_2$CH$_3$, —CH$_2$CH$_2$CH$_3$, —COCH$_3$, —COCH$_2$CH$_3$, —CH$_2$CHOHCH$_2$OH, and —SO$_2$CH$_3$.
6. The compound of claim 1, wherein R$_2$ and R$_6$ are independently selected from the group consisting of hydrogen, fluoro, chloro, and bromo.
7. The compound of claim 1, wherein R$_3$ and R$_5$ are independently selected from the group consisting of hydrogen, fluoro, chloro, bromo, —CH$_3$, —OCH$_3$, —CN, and —NO$_2$.
8. The compound of claim 1, wherein R$_4$ is selected from the group consisting of hydrogen, fluoro, chloro, bromo, —C(CH$_3$)$_3$, —CH$_3$, —CN, and —CF$_3$.
9. The compound of claim 1, wherein R$_7$ and R$_{11}$ are independently selected from the group consisting of hydrogen, fluoro, chloro, —CN, —NO$_2$, and —C$_6$H$_5$.
10. The compound of claim 1, wherein R$_8$ and R$_{10}$ are independently selected from the group consisting of hydrogen, fluoro, chloro, bromo, —CN, —NO$_2$, and —OCH$_3$.

11. The compound of claim 1, wherein $R_9$ is selected from the group consisting of hydrogen, fluoro, chloro, bromo, —OCH$_3$, —CN, —CF$_3$, and —COOCH$_3$.

12. The compound according to claim 1, wherein, the compound is selected from the group consisting of:
cis-[rac]-4-Benzyloxy-4-(4-chloro-phenyl)-3-(3,4-difluoro-benzyloxy)-piperidine;
cis-[rac]-4-Benzyloxy-4-(4-chloro-phenyl)-3-(2,6-difluoro-benzyloxy)-piperidine;
cis-[rac]-4-Benzyloxy-3-(biphenyl-2-ylmethoxy)-4-(4-chloro-phenyl)-piperidine;
cis-[rac]-4-[4-Benzyloxy-4-(4-chloro-phenyl)-piperidin-3-yloxymethyl]-benzonitrile;
cis-[rac]-4-Benzyloxy-4-(4-chloro-phenyl)-3-(3-nitro-benzyloxy)-piperidine;
cis-[rac]-4-Benzyloxy-3-(3-bromo-benzyloxy)-4-(4-chloro-phenyl)-piperidine;
cis-[rac]-4-Benzyloxy-4-(4-chloro-phenyl)-3-(2,4-difluoro-benzyloxy)-piperidine;
cis-[rac]-4-Benzyloxy-3-(2-chloro-4-fluoro-benzyloxy)-4-(4-chloro-phenyl)-piperidine;
cis-[rac]-4-[4-Benzyloxy-4-(4-chloro-phenyl)-piperidin-3-yloxymethyl]-benzoic acid methyl ester;
and cis-[rac]-4-Benzyloxy-4-(4-chloro-phenyl)-3-(3,5-difluoro-benzyloxy)-piperidine.

13. The compound according to claim 1, wherein, the compound is selected from the group consisting of:
cis-[rac]-4-Benzyloxy-3-(3-chloro-2-fluoro-benzyloxy)-4-(4-chloro-phenyl)-piperidine;
cis-[rac]-4-Benzyloxy-4-(4-chloro-phenyl)-3-(2,5-dichloro-benzyloxy)-piperidine;
cis-[rac]-4-Benzyloxy-4-(4-chloro-phenyl)-3-(2,3-difluoro-benzyloxy)-piperidine;
cis-[rac]-4-Benzyloxy-4-(4-chloro-phenyl)-3-(4-trifluoromethyl-benzyloxy)-piperidine;
cis-[rac]-4-Benzyloxy-4-(4-chloro-phenyl)-3-(4-fluoro-benzyloxy)-piperidine;
cis-[rac]-4-Benzyloxy-3-(4-bromo-benzyloxy)-4-(4-chloro-phenyl)-piperidine;
cis-[rac]-4-Benzyloxy-4-(4-chloro-phenyl)-3-(3-fluoro-benzyloxy)-piperidine;
cis-[rac]-2-[4-Benzyloxy-4-(4-chloro-phenyl)-piperidin-3-yloxymethyl]-benzonitrile;
cis-[rac]-3-[4-Benzyloxy-4-(4-chloro-phenyl)-piperidin-3-yloxymethyl]-benzonitrile; and
cis-[rac]-4-Benzyloxy-4-(4-chloro-phenyl)-3-(4,5-dimethoxy-2-nitro-benzyloxy)-piperidine.

14. The compound according to claim 1, wherein, the compound is selected from the group consisting of:
cis-[rac]-4-Benzyloxy-3-but-2-enyloxy-4-(4-chloro-phenyl)-piperidine;
cis-[rac]-4-Benzyloxy-4-(4-chloro-phenyl)-3-pent-2-enyloxy-piperidine;
cis-[rac]-4-Benzyloxy-4-(4-chloro-phenyl)-3-(2,3,6-trifluoro-benzyloxy)-piperidine;
cis-[rac]-4-Benzyloxy-3-butoxy-4-(4-chloro-phenyl)-piperidine;
cis-[rac]-4-Benzyloxy-3-(4-chloro-2-fluoro-benzyloxy)-4-(4-chloro-phenyl)-piperidine;
cis-[rac]-4-Benzyloxy-3-(4-bromo-2-fluoro-benzyloxy)-4-(4-chloro-phenyl)-piperidine;
cis-[rac]-4-Benzyloxy-4-(4-chloro-phenyl)-3-(2,4,6-trifluoro-benzyloxy)-piperidine;
cis-[rac]-4-Benzyloxy-4-(4-chloro-phenyl)-3-(2,4,5-trifluoro-benzyloxy)-piperidine; and
cis-[rac]-4-Benzyloxy-4-(4-chloro-phenyl)-3-(2,3,4-trifluoro-benzyloxy)-piperidine.

15. The compound according to claim 1, wherein, the compound is selected from the group consisting of:
cis-[rac]-3-Benzyloxy-4-(4-chloro-phenyl)-4-(2,4,6-trifluoro-benzyloxy)-piperidine;
cis-[rac]-3-Benzyloxy-4-(4-chloro-phenyl)-4-(2,5-dichloro-benzyloxy)-piperidine;
cis-[rac]-3-Benzyloxy-4-(4-chloro-phenyl)-4-(2,6-dichloro-benzyloxy)-piperidine;
cis-[rac]-3-Benzyloxy-4-(4-chloro-phenyl)-4-(2,6-difluoro-benzyloxy)-piperidine;
cis-[rac]-3-Benzyloxy-4-(4-chloro-phenyl)-4-(3-methoxy-benzyloxy)-piperidine;
cis-[rac]-3-Benzyloxy-4-(4-chloro-phenyl)-4-(2,3,6-trifluoro-benzyloxy)-piperidine;
cis-[rac]-3-Benzyloxy-4-(4-chloro-phenyl)-4-(2-fluoro-benzyloxy)-piperidine; and
cis-[rac]-3-Benzyloxy-4-(4-chloro-phenyl)-4-(2-fluoro-3-methyl-benzyloxy)-piperidine.

16. The compound according to claim 1, wherein, the compound is selected from the group consisting of:
cis-[rac]-4-(4-Chloro-phenyl)-3-(3,4-dichloro-benzyloxy)-4-(4-fluoro-benzyloxy)-piperidine;
cis-[rac]-4-(4-Bromo-benzyloxy)-4-(4-chloro-phenyl)-3-(3,4-dichloro-benzyloxy)-piperidine;
cis-[rac]-4-(4-Chloro-phenyl)-3-(3,4-dichloro-benzyloxy)-4-(2,4-difluoro-benzyloxy)-piperidine;
cis-[rac]-4-(2-Chloro-4-fluoro-benzyloxy)-4-(4-chloro-phenyl)-3-(3,4-dichloro-benzyloxy)-piperidine;
cis-[rac]-4-(2-Bromo-benzyloxy)-4-(4-chloro-phenyl)-3-(3,4-dichloro-benzyloxy)-piperidine;
cis-[rac]-4-(4-tert-Butyl-benzyloxy)-4-(4-chloro-phenyl)-3-(3,4-dichloro-benzyloxy)-piperidine;
cis-[rac]-4-[4-(4-Chloro-phenyl)-3-(3,4-dichloro-benzyloxy)-piperidin-4-yloxymethyl]-benzonitrile;
cis-[rac]-4-(3-Chloro-benzyloxy)-4-($^4$-chloro-phenyl)-3-(3,4-dichloro-benzyloxy)-piperidine;
cis-[rac]-4-(3-Bromo-benzyloxy)-4-(4-chloro-phenyl)-3-(3,4-dichloro-benzyloxy)-piperidine; and
cis-[rac]-4-(4-Chloro-phenyl)-3-(3,4-dichloro-benzyloxy)-4-(2-fluoro-benzyloxy)-piperidine.

17. The compound according to claim 1, wherein, the compound is selected from the group consisting of:
cis-[rac]-4-(4-Chloro-phenyl)-3-(3,4-dichloro-benzyloxy)-4-(3,5-difluoro-benzyloxy)-piperidine;
cis-[rac]-4-(3-Chloro-2-fluoro-benzyloxy)-4-(4-chloro-phenyl)-3-(3,4-dichloro-benzyloxy)-piperidine;
cis-[rac]-4-(4-Chloro-phenyl)-3-(3,4-dichloro-benzyloxy)-4-(2,3-difluoro-benzyloxy)-piperidine;
cis-[rac]-4-(4-Chloro-phenyl)-3-(3,4-dichloro-benzyloxy)-4-(4-trifluoromethyl-benzyloxy)-piperidine;
cis-[rac]-4-(4-Chloro-phenyl)-3-(3,4-dichloro-benzyloxy)-4-(3-fluoro-benzyloxy)-piperidine;
cis-[rac]-3-[4-(4-Chloro-phenyl)-3-(3,4-dichloro-benzyloxy)-piperidin-4-yloxymethyl]-benzonitrile;
cis-[rac]-4-(2-Chloro-benzyloxy)-4-(4-chloro-phenyl)-3-(3,4-dichloro-benzyloxy)-piperidine; and
cis-[rac]-4-(4-Chloro-phenyl)-3-(3,4-dichloro-benzyloxy)-4-(4-methyl-benzyloxy)-piperidine.

18. The compound according to claim 1, wherein, the compound is selected from the group consisting of:

cis-[rac]-4-(4-Chloro-phenyl)-3,4-bis-(2,4-difluoro-benzyloxy)-piperidine; and cis-[rac]-4-(4-Chloro-phenyl)-3,4-bis-(3-nitro-benzyloxy)-piperidine.

19. The compound according to claim 1, wherein, the compound is selected from the group consisting of:

cis-[rac]-1-[4-Benzyloxy-4-(4-chloro-phenyl)-3-(2,4-difluoro-benzyloxy)-piperidin-1-yl]-ethanone;

cis-[rac]-1-[4-Benzyloxy-3-(3-bromo-benzyloxy)-4-(4-chloro-phenyl)-piperidin-1-yl]-ethanone;

cis-[rac]-1-[4-Benzyloxy-3-(2-chloro-4-fluoro-benzyloxy)-4-(4-chloro-phenyl)-piperidin-1-yl]-ethanone;

cis-[rac]-1-[4-Benzyloxy-4-(4-chloro-phenyl)-3-(3,5-difluoro-benzyloxy)-piperidin-1-yl]-ethanone;

cis-[rac]-1-[4-Benzyloxy-3-(3-chloro-2-fluoro-benzyloxy)-4-(4-chloro-phenyl)-piperidin-1-yl]-ethanone;

cis-[rac]-1-[4-Benzyloxy-4-(4-chloro-phenyl)-3-(3,4-dichloro-benzyloxy)-piperidin-1-yl]-ethanone;

cis-[rac]-1-[4-Benzyloxy-4-(4-chloro-phenyl)-3-(4-fluoro-benzyloxy)-piperidin-1-yl]-ethanone;

cis-[rac]-1-[4-Benzyloxy-3-(4-bromo-benzyloxy)-4-(4-chloro-phenyl)-piperidin-1-yl]-ethanone;

cis-[rac]-1-[4-Benzyloxy-4-(4-chloro-phenyl)-3-(3-fluoro-benzyloxy)-piperidin-1-yl]-ethanone;

and cis-[rac]-3-[1-Acetyl-4-benzyloxy-4-(4-chloro-phenyl)-piperidin-3-yloxymethyl]-benzonitrile.

20. The compound according to claim 1, wherein, the compound is selected from the group consisting of:

cis-[rac]-1-[4-Benzyloxy-4-(4-chloro-phenyl)-3-(2,6-difluoro-benzyloxy)-piperidin-1-yl]-ethanone;

cis-[rac]-1-[4-Benzyloxy-4-(4-chloro-phenyl)-3-(3-nitro-benzyloxy)-piperidin-1-yl]-ethanone;

cis-[rac]-1-[4-Benzyloxy-4-(4-chloro-phenyl)-3-(2,3,4-trifluoro-benzyloxy)-piperidin-1-yl]-ethanone; and cis-[rac]-1-[4-(4-Chloro-phenyl)-3-(3,4-dichloro-benzyloxy)-4-(2-fluoro-benzyloxy)-piperidin-1-yl]-ethanone.

21. The compound according to claim 1, wherein, the compound is selected from the group consisting of:

cis-[rac]-1-[4-Benzyloxy-4-(4-chloro-phenyl)-3-(2,3,4-trifluoro-benzyloxy)-piperidin-1-yl]-propan-1-one;

cis-[rac]-1-[4-Benzyloxy-4-(4-chloro-phenyl)-3-(3,4-dichloro-benzyloxy)-piperidin-1-yl]-propan-1-one; and cis-[rac]-4-Benzyloxy-3-(4-bromo-benzyloxy)-4-(4-fluoro-phenyl)-piperidine.

22. The compound according to claim 1, wherein, the compound is selected from the group consisting of:

cis-[rac]-4-Benzyloxy-4-(4-chloro-phenyl)-3-(3,4-dichloro-benzyloxy)-1-ethyl-piperidine;

cis-[rac]-4-Benzyloxy-4-(4-chloro-phenyl)-3-(3,4-dichloro-benzyloxy)-1-propyl-piperidine;

cis-[rac]-3-[4-Benzyloxy-4-(4-chloro-phenyl)-3-(2,3,4-trifluoro-benzyloxy)-piperidin-1-yl]-propane-1,2-diol;

cis-[rac]-3-[4-Benzyloxy-3-(4-bromo-benzyloxy)-4-(4-chloro-phenyl)-piperidin-1-yl]-propane-1,2-diol; and cis-[rac]-3-[4-Benzyloxy-4-(4-chloro-phenyl)-3-(2,3,4-trifluoro-benzyloxy)-piperidin-1-yl]-methane sulfonyl.

23. A pharmaceutical composition comprising a therapeutically effective amount of a compound of claim 1 and a pharmaceutically acceptable carrier or excipient.

24. A method for treating cancer comprising administering to a patient in need of such treatment a therapeutically effective amount of a compound of claim 1.

25. The method of claim 24, wherein the cancer is breast or colon cancer.

* * * * *